United States Patent
Buck, Jr. et al.

(10) Patent No.: US 9,594,045 B2
(45) Date of Patent: Mar. 14, 2017

(54) METHODS OF DETECTING HIGH ANTIOXIDANT LEVELS DURING ELECTROCHEMICAL MEASUREMENTS AND FAILSAFING AN ANALYTE CONCENTRATION THEREFROM

(71) Applicant: Roche Diabetes Care, Inc., Indianapolis, IN (US)

(72) Inventors: Harvey B. Buck, Jr., Indianapolis, IN (US); Scott E. Carpenter, Pendleton, IN (US); Zheng Zheng Pan, Plano, TX (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 14/852,114

(22) Filed: Sep. 11, 2015

(65) Prior Publication Data
US 2016/0011140 A1    Jan. 14, 2016

Related U.S. Application Data

(63) Continuation of application No. PCT/EP2014/054962, filed on Mar. 13, 2014.
(Continued)

(51) Int. Cl.
*G01N 27/327* (2006.01)

(52) U.S. Cl.
CPC ................ *G01N 27/3274* (2013.01)

(58) Field of Classification Search
CPC .............. G01N 27/327–27/3274; G01N 27/48
See application file for complete search history.

(56) References Cited

U.S. PATENT DOCUMENTS 4,795,542 A * 1/1989 Ross ................ G01N 27/3271
                                                        204/403.09
5,589,045 A * 12/1996 Hyodo ............. G01N 33/48792
                                                        204/403.11
(Continued)

FOREIGN PATENT DOCUMENTS

EP    1156324 A1    11/2001
EP    2042865 A2    4/2009
(Continued)

OTHER PUBLICATIONS

Mugweru et al. "Redox Protein-Polymer Films for Simultaneous Determination of Ascorbic Acid and Hydrogen Peroxide", Analytical Sciences Sep. 2008 vol. 24 pp. 1105-1110.*
(Continued)

*Primary Examiner* — Alexander Noguerola

(57) ABSTRACT

Methods are disclosed for measuring an analyte concentration in a fluidic sample. Such methods further allow one to provide an error code or correct and/or compensate for interferents such as an antioxidant before providing an analyte concentration. The measurement methods utilize information obtained from test sequences having at least one DC block, such as a slow-ramped bi-polar waveform, where a closed circuit condition is maintained during the DC block. The methods use information relating to status of a redox mediator feature during the electrochemical analysis to provide an antioxidant failsafe if the antioxidant is interfering with the analyte concentration. Also disclosed are devices, apparatuses and systems incorporating the various measurement methods.

33 Claims, 25 Drawing Sheets

Related U.S. Application Data

(60) Provisional application No. 61/800,952, filed on Mar. 15, 2013.

(56) References Cited

U.S. PATENT DOCUMENTS

| | | | | |
|---|---|---|---|---|
| 5,665,215 | A * | 9/1997 | Bussmann | C12Q 1/001 |
| | | | | 204/401 |
| 6,984,307 | B2 * | 1/2006 | Zweig | C12Q 1/005 |
| | | | | 204/403.04 |
| 8,500,990 | B2 * | 8/2013 | Pei | C12Q 1/006 |
| | | | | 204/403.14 |
| 2003/0060692 | A1 | 3/2003 | Ruchti et al. | |
| 2003/0104119 | A1 * | 6/2003 | Wilson | C12Q 1/001 |
| | | | | 427/2.1 |
| 2004/0157339 | A1 | 8/2004 | Burke et al. | |
| 2005/0279631 | A1 | 12/2005 | Celentano | |
| 2007/0102292 | A1 | 5/2007 | Dreibholz et al. | |
| 2009/0030641 | A1 | 1/2009 | Fjield et al. | |
| 2011/0139617 | A1 * | 6/2011 | Fransaer | C07K 17/00 |
| | | | | 204/403.14 |

FOREIGN PATENT DOCUMENTS

| | | |
|---|---|---|
| EP | 2138841 A2 | 12/2009 |
| EP | 2261646 B1 | 7/2015 |
| WO | 9932881 A1 | 7/1999 |
| WO | 0121827 A1 | 3/2001 |
| WO | 03060154 A2 | 7/2003 |
| WO | 2006109279 A2 | 10/2006 |
| WO | 2007100651 A1 | 9/2007 |
| WO | 2008036516 A1 | 3/2008 |
| WO | 2009075951 A1 | 6/2009 |
| WO | 2012134890 A1 | 10/2012 |

OTHER PUBLICATIONS

Introduction to voltammetry using CV Sim, N. Murer and J.-P. Dlard, BioLogic Science Instruments, pp. 1-40, publication date unknown.*

Gunasingham; et al., "Pulsed amperometric detection of glucose using a mediated enzyme electrode", Journal of Electroanalytical Chemistry and Interfacial Electrochemistry, Jul. 25, 1990, vol. 287, No. 2, pp. 349-362.

* cited by examiner

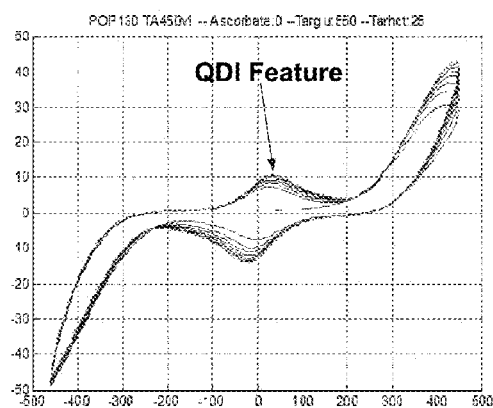
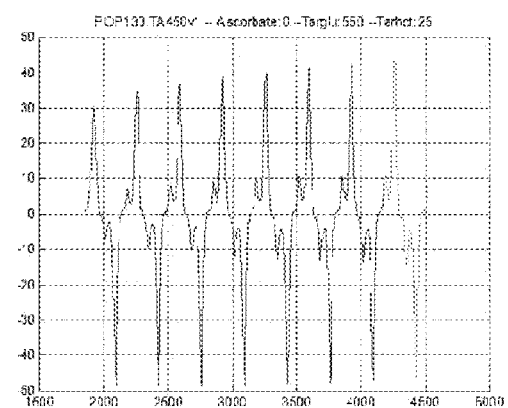
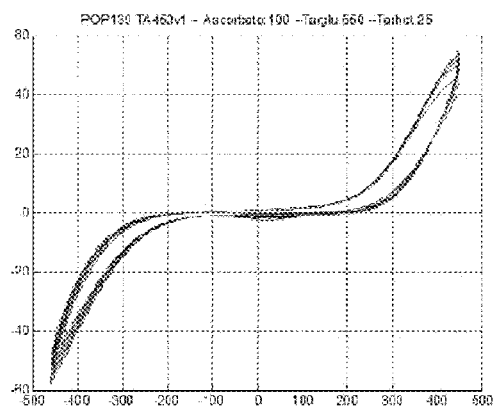
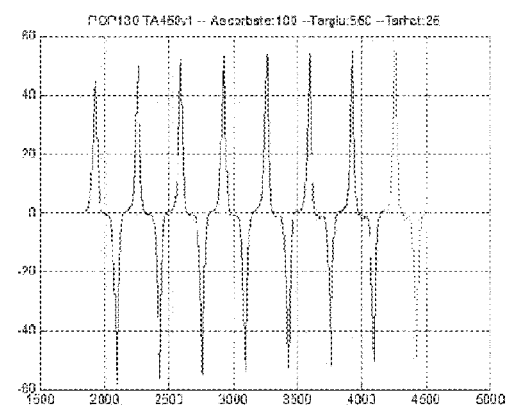
FIG. 5A
FIG. 5B

A.

B.

C.

D.

E.

F.

METHODS OF DETECTING HIGH ANTIOXIDANT LEVELS DURING ELECTROCHEMICAL MEASUREMENTS AND FAILSAFING AN ANALYTE CONCENTRATION THEREFROM

CROSS-REFERENCE TO RELATED APPLICATIONS

This patent application is a continuation of Intl Patent Application No. PCT/EP2014/054962 (filed 13 Mar. 2014), which claims priority to and the benefit of U.S. Provisional Patent Application No. 61/800,952 (filed 15 Mar. 2013). Each patent application is incorporated herein by reference as if set forth in its entirety.

TECHNICAL FIELD

This disclosure relates generally to mathematics and medicine, and more particularly, it relates to methods of electrochemically measuring an analyte concentration in a fluidic sample and failsafing the analyte concentration if a predetermined antioxidant level is detected or if a reagent failure is detected.

BACKGROUND

Significant benefits can be realized from electrochemically measuring analytes in fluidic samples (i.e., biological or environmental). For example, diabetic treatment with self-monitoring blood glucose (SMBG) devices and systems contributes to improving glycemic control and attenuating diabetes-related morbidity. Therefore, the accuracy of SMBG devices and systems is important for optimal glycemic control.

The accuracy, however, of present methods of electrochemically measuring analytes such as glucose can be negatively affected by a number of interferents including antioxidants or other reducing agents. Because of their benefits, there is an increasing number of medical uses, as well as off-label therapies and alternative medicine procedures, in which megadoses of antioxidants are administered by injection or intravenously. For example, burn patents often are treated with parenteral doses of ascorbate, resulting in blood plasma levels of 40 mg/dL or more. There also are alternative cancer therapies that prescribe much larger doses, resulting in ascorbate levels as high as 400 mg/dL. Unfortunately, high doses of antioxidants such as ascorbate can interfere with the electrochemical response of SMGB devices and systems and can cause them to report falsely elevated glucose concentrations, which presents a significant disadvantage for an individual with diabetes receiving an antioxidant therapy. Specifically, if an individual is in a euglycemic state, but responds to the falsely elevated glucose concentration by administering insulin, this could result in hypoglycemia and/or death. The Food and Drug Administration suggests that ascorbate interference exists for some electrochemical assays even at 3 mg/dL of ascorbate.

Current electrochemical SMBG methods, devices and systems provide individuals having diabetes advantages with respect to convenience; however, there remains a need for improved methods of electrochemically measuring an analyte in a fluid sample with additional quality checks for the presence of interferents such as an antioxidant or for detecting a failure with the biosensor reagent system.

BRIEF SUMMARY

In view of the disadvantages noted above, the disclosure describes methods of detecting an interferent and in some instances failsafing an electrochemical measurement of an analyte that may be biased. The methods are based upon an inventive concept that includes using information derived from an electrical test sequence that provides at least one direct current (DC) response. The test sequence is designed to provide specific information about an impact of an interferent such as an antioxidant in the fluidic sample on a redox mediator of an electrochemical analyte measurement system. For example, information such as current response, shape and/or magnitude from at least one DC block can be used to failsafe against falsely elevated analyte concentrations due to the antioxidant. In particular, the methods use information relating to a redox mediator status derived from at least one DC block to discriminate between antioxidant levels at which the analyte prediction bias of an electrochemical system is acceptable and antioxidant levels at which the analyte prediction bias is clinically unacceptable. The methods therefore aid in ensuring patient safety. Specifically, it has been found that antioxidants can increase an amount of a reduced form of some redox mediators, thereby falsely increasing current detected during the electrochemical analysis. Moreover, it has been found that information pertaining to a redox mediator status during an electrochemical measurement can be used to detect a reagent layer failure. The inventive concept therefore provides certain advantages, effects, features and objects when compared to known methods of measuring an analyte concentration (or value) in a fluidic sample and thereby attenuate incidents of erroneously reporting falsely elevated analyte concentration due to antioxidants and/or reagent failures.

In one aspect, an electrochemical analysis method is provided for measuring, determining, calculating or otherwise predicting an analyte concentration in a fluidic sample having one or more interferents such as an antioxidant, where the method includes an antioxidant failsafe. The method can include the steps of providing a test sequence of at least one DC block to the fluidic sample and measuring the response information thereto, where the at least one DC block is designed to elicit specific information about different aspects of the sample and/or the biosensor, including a redox mediator status.

In some instances, the test sequence also can include at least one AC block. In other instances, the test sequence also can include a second DC block. In still other instances, the test sequence includes the at least one AC block, the at least one DC block and the second DC block.

The at least one DC block is a slow-ramped bi-polar potential (SRBP) waveform that alternates or cycles between a plurality of short-duration positive potential intervals and negative potential intervals optimized for detecting an antioxidant such as ascorbate, the optimization pertaining to segment duration, ramped transitions between the intervals, number of current responses measured during each interval, and where in each interval current response measurements are taken.

In some instances, the SRBP waveform can include from about one (1) interval to about ten (10) intervals.

In some instances, the SRBP waveform can be at a potential that alternates or cycles between about −450 mV to about +450 mV in a closed circuit. Moreover, each of the SRBP waveform intervals can be applied for about 100 msec to about 5 sec. Furthermore, the ramp rate can be from about 0.500 mV/msec to ≤about 45 mV/msec.

In some instances, the SRBP waveform intervals can be applied at the same ramp rates. In other instances, the intervals can be applied at different ramp rates. In still other instances, each interval has its own ramp rate.

In some instances, the SRBP waveform can be a triangular waveform, trapezoidal waveform, sinusoidal waveform or combinations thereof.

When included, the second DC block can be a continuous, unipolar, pulsed excitation waveform (i.e., the potential is applied and controlled throughout the DC block in a closed circuit), which is in contrast to some pulsed amperometric methods that employ an open circuit between excitation pulses. The DC block includes a plurality of short-duration excitation pulses and recovery pulses optimized for detecting an analyte such as glucose, the optimization pertaining to pulse duration, ramped transitions between the excitation pulse and recovery pulse, number of current responses measured during each pulse, and where in each pulse current response measurements are taken.

In some instances, the second DC block can include at least one (1) pulse to about ten (10) pulses. The second DC block can be at a potential that alternates between about 0 mV to about +450 mV in a closed circuit. Moreover, each of the DC pulses can be applied for about 50 msec to about 500 msec. Furthermore, the ramp rate can be from about 10 mV/msec to about 50 mV/msec.

In some instances, the second DC block pulses can be applied at the same ramp rate. In other instances, the pulses can be applied at different ramp rates.

In some instances, the second DC block precedes the at least one DC block. For example, a pulsed DC block may precede the SRBP waveform.

When included, the AC block can be a block of low-amplitude AC signals. In some instances, the AC block is applied before the at least one DC block, after the at least one DC block, or interspersed therewith. Likewise, and in other instances, the AC block is applied before the at least one DC block and the second DC block, after the at least one DC block and the second DC block, or interspersed therewith. In still other instances, the test sequence includes the at least one AC block, the at least one DC block and the second DC block.

In addition, the method can include a step of providing a qualitative or quantitative antioxidant failsafe based at least in part upon response information to the SRBP waveform, such as a triangular, trapezoidal, sinusoidal waveform, or even a combination thereof. For example, the failsafe can be as simple as checking for an existence or absence of a redox mediator feature, including a ratio thereof. As such, the methods use information relating to status of the redox mediator feature during the electrochemical analysis to provide an antioxidant failsafe if the antioxidant is interfering with the analyte concentration.

In some instances, the antioxidant is ascorbate, the analyte is glucose, and the redox mediator is a nitrosoanaline (NA)-derived redox mediator.

In another aspect, an electrochemical analysis method is provided for measuring, determining, calculating or otherwise predicting an analyte concentration in a fluidic sample, where the method includes a reagent layer health failsafe. The method can include the steps of providing a test sequence of at least one DC block to the fluidic sample as described above and measuring response information thereto. The reagent layer health failsafe, however, includes checking for a simple existence or absence of a feature of an oxidized form of the redox mediator ($M_{ox}$) and/or a feature of a reduced form of the redox mediator ($M_{red}$) as a basis for the reagent layer health failsafe.

In some instances, the analyte is glucose, and the redox mediator is a nitrosoanaline (NA)-derived redox mediator.

In either aspect above, where the measurement indicates a potential for a clinically significant bias, the analyte concentration is not displayed but instead is failsafed (i.e., not reported) with an appropriate message of suspected interference, reagent layer failure or even a general biosensor failure.

In view of the foregoing, devices, apparatuses and systems used in connection with electrochemical analysis are provided that incorporate one or more of the measurement methods disclosed herein. These devices, apparatuses and systems can be used to determine concentration of analytes including, but not limited to, amino acids, antibodies, bacteria, carbohydrates, drugs, lipids, markers, nucleic acids, peptides, proteins, toxins, viruses and other analytes, as well as combinations thereof, in the presence of an antioxidant. In some instances, the antioxidant is ascorbate, and the analyte is glucose.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein:

FIG. 3B is a more detailed test sequence and also includes exemplary current responses.

FIGS. 5A-B show comparisons of two blood samples, each containing 550 mg/dL glucose at 25% Hct; one containing no ascorbate (upper plots); and one containing 100 mg/dL ascorbate (lower plots). For each sample, a cyclic voltammagram (CV; y-axis is current in nA and x-axis is applied potential in mV) is shown on the left plots of FIG. 5A, and the measured current response (y-axis is current in nA and x-axis is time in msec) is shown on the right plots of FIG. 5B.

FIG. 8B is a more detailed test sequence and also includes exemplary current responses.

FIG. 14A shows a glutathione prediction for PLS Model 1; FIG. 14B shows a glucose prediction for PLS Model 2.

Figure 1:
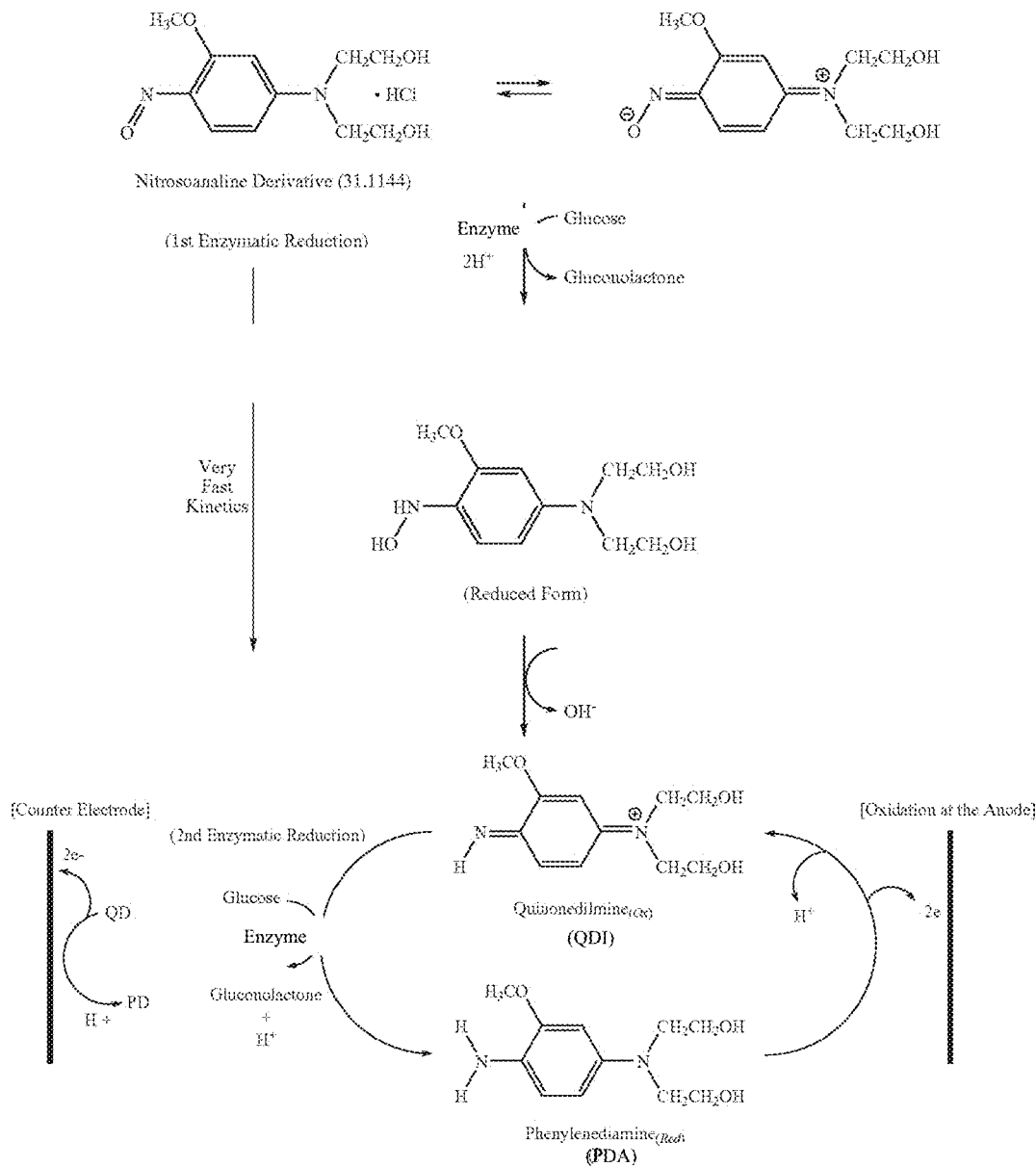
FIG. 1 shows an exemplary electrochemical reaction and its electron transfer pathway from a NA-derived redox mediator to a working electrode of an exemplary analyte measurement system.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments above and the claims below. Reference should therefore be made to the embodiments above and claims below for interpreting the scope of the inventive concept. As such, it should be noted that the embodiments described herein may have advantages, effects, features and objects useful in solving other problems.

DESCRIPTION OF PREFERRED EMBODIMENTS

The methods, devices, apparatuses and systems now will be described more fully hereinafter with reference to the accompanying drawings, in which some, but not all embodiments of the inventive concept are shown. Indeed, the inventive concept may be embodied in many different forms and should not be construed as limited to the embodiments set forth herein; rather, these embodiments are provided so that this disclosure will satisfy applicable legal requirements.

Likewise, many modifications and other embodiments of the methods, devices, apparatuses and systems described herein will come to mind to one of skill in the art to which the disclosure pertains having the benefit of the teachings presented in the foregoing descriptions and the associated drawings. Therefore, it is to be understood that the inventive concept is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the present methods, devices, apparatuses and systems, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

Overview

Analyte measurement methods are disclosed herein that use information derived from AC and/or DC current responses to provide an analyte concentration in a reliable manner. In particular, the methods use information relating to status of a redox mediator such as a NA-derived redox mediator obtained from at least one DC block to discriminate between antioxidant levels at which the analyte prediction bias of an electrochemical system is acceptable and antioxidant levels at which the analyte prediction bias is clinically unacceptable is essential to ensure patient safety. The measuring methods therefore can be used to reduce the effects of interferents such as an antioxidant on an analyte concentration measurement, thereby providing a more "true" analyte concentration or even preventing a reporting of a falsely elevated analyte concentration.

In the examples below, a NA-derived redox mediator was used. However, based upon the general teachings herein, one of skill in the art will understand how to select appropriate potential differences for the applied potentials for regions of excitation of diffusion-limited current and regions of recovery or current that is not diffusion-limited based upon a selected redox mediator. Here, the selection of about +450 mV and about 0 mV is appropriate for excitation and recovery pulses with NA-derived redox mediators. It is understood that even for such NA-derived redox mediators, there are acceptable ranges of greater applied potential for diffusion-limited current and similarly and there are acceptable ranges for the applied recovery potential. Each redox mediator therefore will have a specific redox potential and characteristic electron transfer kinetics from which one of skill in the art could select the appropriate potential differences for excitation or recovery.

As used herein, "nitrosoaniline-derived redox mediator" or "NA-derived redox mediator" means a substituted nitrosoanline compound as described in, for example, U.S. Pat. No. 5,122,244. An example of a NA-derived redox mediator is N,N-bis(hydroxyethyl)-3-methoxy-4-nitrosoaniline hydrochloride. Other examples of NA-derived redox mediators include, but are not limited to, 4,6-dinitro-2-nitrosoaniline, N'-bis-(2-hydroxyethyl)-p-nitrosoaniline, N,N'-dimethyl-p-nitrosoaniline, N,N'-diethyl-p-nitrosoaniline, N-methyl-N'-(4-nitrosophenyl)-piperazine, N-(2-hydroxyethyl)-5-nitrosoindoline, 2,4-dimethoxy-nitrosobenzene, N,N'-bis-(2-methoxyethyl)-4-nitrosoaniline, N-(4-nitrosophenyl)-morpholine, N-(2,2-diethoxy-ethyl)N'-(4-nitrosophenyl)-piperazine, p-nitrosophenol, 3-methoxy-4-nitrosophenol, N-(2-hydroxyethyl)-N'-p-nitrosophenyl-piperazine, N,N-bis-(2-hydroxyethyl)-p-nitrosoaniline, o-methoxy-N,N-bis-(2-hydroxyethyl)]-p-nitrosoaniline, p-hydroxynitrosobenzene, N-methyl-N'-(4-nitrosophenyl)-piperazine, p-quinone dioxime, N,N-dimethyl-p-nitrosoaniline, N,N-diethyl-p-nitrosoaniline, N-(4-nitrosophenyl)-morpholine, N-benzyl-N-(5'-carboxypentyl)-p-nitrosoaniline, N,N-dimethyl-4-nitroso-1-naphthylamine, N,N,3-trimethyl-4-nitrosoaniline, N-(2-hydroxyethyl)-5-nitrosoindoline, N,N-bis-(2-hydroxyethyl)-3-chloro-4-nitrosoaniline, 2,4-dimethoxy-nitrosobenzene, N,N-bis-(2-methoxyethyl)-4-nitrosoaniline, 3-methoxy-4-nitrosophenol, N-(2-hydroxyethyl)-6-nitroso-1,2,3 tetrahydroquinoline, N,N-dimethyl-3-chloro-4-nitrosoaniline, N,N-bis-(2-hydroxyethyl)-3-fluoro-4-nitrosoaniline, N,N-bis-(2-hydroxyethyl)-3-methylthio-4-nitrosoaniline, N-(2-hydroxyethyl)-N-(2-(2-methoxyethoxy)-ethyl)-4-nitrosoaniline, N-(2-hydroxyethyl)-N-(3-methoxy-2-hydroxy-1-propyl)-4-nitrosoaniline, N-(2-hydroxyethyl)-N-(3-(2-hydroxyethoxy)-2-hydroxy-1-propyl)-4-nitrosoaniline, N-(2-hydroxyethyl)-N-(2-(2-hydroxyethoxy)-ethyl)-4-nitrosoanaline, 3-(4'-chloro-phenylimino)-3H-phenothiazine, 3-(4'-diethylamino-phenylimino)-3H-phenothiazine, 3-(4'ethyl-phenylimino)-3H-phenothiazine, 3-(4'-trifluoromethyl-phenylimino)-3H-phenothiazine, 3-(4'-methoxycarbonyl-phenylimino)-3H-phenothiazine, 3-(4'-nitro-phenylimino)-3H-phenothiazine, 3-(4'-methoxy-phenylimino)-3H-phenothiazine, 7-acetyl-3-(4'-methoxy-carbonylphenylimino)-3H-phenothiazine, 7-trifluoromethyl-3-(4'-methoxycarbonylphenylimino)-3H-phenothiazine, 3-(4'-omega-carboxy-n-butyl-phenylimino)-3H-phenothiazine, 3-(4'-aminomethyl-phenylimino)-3H-phenothiazine, 3-(4'-(2"-(5"-(p-aminophenyl)-1,3,4-oxadiazoyl)phenylimino)-3H-phenothiazine, 3-(4'-β-aminoethyl-phenylimino)-3H-phenothiazine, 6-(4'-ethylphenyl)amino-3-(4'-ethyl-phenylimino)-3H-phenothiazine, 6-(4'-[2-(2-ethanoloxy)ethoxy]ethoxyphenyl)amino-3-(4'-[2-(2-ethanoloxy)ethoxy]ethoxy-phenylimino-3H-phenothiazine, 3-(4'-[2-(2-ethanoloxy)ethoxy]ethoxy-phenylimino-3H-phenothiazine, 3-(4'-phenylimino)-3H-phenothiazineboronic acid, (3-(3',5'-dicarboxy-phenylimino)-3H-phenothiazine, 3-(4'-carboxy-phenylimino)-3H-phenothiazine, 3-(3',5'-dicarboxy-phenylimino)-3H-phenoxazine, 3-(3',5'-phenylimino)-3H-phenothiazinedisulfonic acid, 3-(3-phenylimino)-3H-phenothiazinesulfonic acid, and combinations thereof. See also, U.S. Pat. Nos. 5,122,244 and 5,286,362.

As used herein, "antioxidant" or "antioxidants" means a compound or substance that can prevent damage caused by unstable molecules, such as free radicals and active oxygen species (i.e., prevents damage caused by oxidation from singlet oxygen, hydrogen peroxide, hydroxyl radical, etc.). As reducing agents, antioxidants may exert their effects in two ways: (1) as direct-acting antioxidants that inactivate oxidative agents such as free radicals; and (2) as indirect agents that can modulate the function, activity or level of other antioxidants or antioxidant mechanisms. Of interest herein are antioxidants that reduce a redox mediator in an electrochemical enzymatic analyte measurement system. Examples of antioxidants typically used in a clinical setting include, but are not limited to, ascorbate (also known as Vitamin C or ascorbic acid), citric acid, deferoxamine (DFO), glutathione, N-acetylcysteine (NAC), pyrrolidine dithiocarbamate (PDTC), trylizad-mesylate (TLM) and uric acid.

FIG. 1 shows an exemplary electrochemical reaction and electron transfer pathway from a NA-derived redox mediator to the working electrode of an exemplary analyte measurement system. The electrochemical reaction in FIG. 1 may occur in an electrochemical biosensor 20 in response to an analyte such as glucose, where NA forms an intermediate that quickly converts to QDI and then is reduced to PDA. Each molecule of PDA can be oxidized at the working electrode to liberate two electrons, which are detected by the working electrode, also resulting in the cyclical re-formation of QDI. Ascorbate, being an effective reducing agent, reacts rapidly with QDI, thereby increasing the amount of PDA, resulting in a higher current being detected at the working electrode. It is this perceived higher current that is then translated into a falsely-elevated blood glucose (bG) concentration. One of skill in the art will appreciate that a similar effect may be caused by any potential interferent that is an effective reducing agent reacting rapidly with QDI to produce excess PDA in this manner. Generally stated, a falsely-elevated bG concentration may result from any interferent that is effective at rapidly converting $M_{ox}$ to produce an artificially high amount of the corresponding $M_{red}$.

More specifically, and as shown in FIG. 1, the NA-derived redox mediator reacts with a reduced form of an enzyme (e.g., flavin adenine dinucleotide-dependent glucose dehydrogenase (FAD-GDH) or pyrroloquinoline quinone glucose dehydrogenase (PQQ-GDH)) that catalyzes the oxidation of glucose in the presence of an electron acceptor to produce a reduced NA-derived redox mediator that quickly undergoes hydrolysis to form QDI. QDI then reacts through a second enzymatic reduction to form PDA. As above, each molecule of PDA can be oxidized to liberate two electrons, which are detected by the working electrode, also resulting in the cyclical re-formation of QDI. Ascorbate, however, causes a perceived higher current by increasing the amount of PDA, which is then translated into a falsely-elevated bG concentration.

It shall be understood, however, that while certain exemplary embodiments deal with biosensors that use NA as the redox mediator, other reagent layer chemistries and redox mediators can utilize the same inventive concept such as the one described herein. It therefore shall further be appreciated that the electrochemical reaction of FIG. 1 and the use of a NA-derived redox mediator are non-limiting examples, and that the methods, devices, apparatuses and systems disclosed herein may be used in connection with a plurality of enzymes and different redox mediators.

Advantageously, the measurement methods provide an ability to discriminate between antioxidant levels at which the analyte prediction bias of an electrochemical system is acceptable and antioxidant levels at which the antioxidant prediction bias is clinically unacceptable to ensure patient safety. Such methods may provide this functionality without the need for information that is different from that which is used for analyte prediction (e.g., glucose prediction). In some instances, an approach is used for discriminating antioxidant levels that result in a biased analyte estimate that is either acceptable or unacceptable from a clinical perspective. Other instances implement this capability in the form of an antioxidant failsafe within the SMBG meter. If the failsafe is triggered, a meter can be configured to deliver an error code or a specific antioxidant interference error message rather than an inaccurate analyte concentration.

For example, the failsafe could include direct messaging such as: "An antioxidant level was detected to be greater than the acceptable range for this blood glucose assay and thus a glucose value cannot be reported." This could result in a health care professional follow up to determine the cause and find a suitable clinical analyzer that may not have a bias due to this antioxidant.

Other instances include a "reagent layer health" or "chemistry health" failsafe for determining whether the reagent layer and redox mediator of the biosensor are working properly, or whether the reagent layer is compromised by any number of different interferents. As such, the failsafe could include direct messaging such as: "A reagent layer health error was detected on the biosensor and thus a glucose value cannot be reported" or "A chemistry health error was detected on the biosensor and thus a glucose value cannot be reported." This could result in a user selected a new biosensor to repeat the electrochemical measurement.

As used herein, "reagent layer health" or "chemistry health" means an ability of a test system reagent, mediator and/or mediator precursor in contact with a test sample to provide a desired electrochemical response to an applied test signal, which is not unacceptably impacted or impaired by any of a plurality of interferents either known or unknown.

The measurement methods disclosed herein largely utilize amperometry; however, it is contemplated that the methods can be used with other electrochemical measurement methods (e.g., coulometry, potentiometry or voltammetry). Additional details regarding exemplary electrochemical measurement methods are disclosed in, for example, U.S. Pat. Nos. 4,008,448; 4,225,410; 4,233,029; 4,323,536; 4,891,319; 4,919,770; 4,963,814; 4,999,582; 4,999,632; 5,053,199; 5,108,564; 5,120,420; 5,122,244; 5,128,015; 5,243,516; 5,288,636; 5,352,351; 5,366,609; 5,385,846; 5,405,511; 5,413,690; 5,437,999; 5,438,271; 5,508,171; 5,526,111; 5,627,075; 5,628,890; 5,682,884; 5,727,548; 5,762,770; 5,858,691; 5,997,817; 6,004,441; 6,054,039; 6254736; 6,270,637; 6,645,368; 6,662,439; 7,073,246; 7,018,843; 7,018,848; 7,045,054; 7,115,362; 7,276,146; 7,276,147; 7,335,286; 7,338,639; 7,386,937; 7,390,667; 7,407,811; 7,429,865; 7,452,457; 7,488,601; 7,494,816; 7,545,148; 7,556,723; 7,569,126; 7,597,793; 7,638,033; 7,731,835; 7,751,864; 7,977,112; 7,981,363; 8,148,164; 8,298,828; 8,329,026; 8,377,707; and 8,420,404, as well as RE36268, RE42560, RE42924 and RE42953.

Advantageously, the methods described herein can be incorporated into SMBG devices, apparatuses and systems to more accurately and quickly report an analyte concentration, such as a glucose concentration, especially a blood glucose concentration.

Moreover, the measurement methods can be implemented using advanced microprocessor-based algorithms and processes that result in dramatically improved system performance. These measurement methods also offer flexibility and number of ways to create algorithms that can achieve improved performance such as 10/10 performance. As used herein, "10/10 performance" means that a measured bG value is within about ±10% of the actual bG value for bG concentrations >100 mg/dL, and within ±10 mg/dL of the actual bG value for bG concentrations <100 mg/dL.

Details regarding additional electrochemical measurement methods that may be useful in performing the methods disclosed herein can be found in the following co-filed and co-pending patent applications titled: "METHODS OF SCALING DATA USED TO CONSTRUCT BIOSENSOR ALGORITHMS AS WELL AS DEVICES, APPARATUSES AND SYSTEMS INCORPORATING THE SAME" (Int'l Patent Application No. PCT/EP2014/054952); "METHODS OF ELECTROCHEMICALLY MEASURING AN ANALYTE WITH A TEST SEQUENCE HAVING A PULSED DC BLOCK AS WELL AS DEVICES, APPARATUSES AND SYSTEMS INCORPORATING THE SAME" (Int'l Patent Application No. PCT/EP2014/054965); "METHODS OF FAILSAFING ELECTROCHEMICAL MEASUREMENTS OF AN ANALYTE AS WELL AS DEVICES, APPARATUSES AND SYSTEMS INCORPORATING THE SAME" (Int'l Patent Application No. PCT/EP2014/054955); "METHODS OF USING INFORMATION FROM RECOVERY PULSES IN ELECTROCHEMICAL ANALYTE MEASUREMENTS AS WELL AS DEVICES, APPARATUSES AND SYSTEMS INCORPORATING THE SAME" (Int'l Patent Application No. PCT/EP2014/054943); and "DESCRIPTOR-BASED METHODS OF ELECTROCHEMICALLY MEASURING AN ANALYTE AS WELL AS DEVICES, APPARATUSES AND SYSTEMS INCOPORATING THE SAME" (Int'l Patent Application No. PCT/EP2014/054956).

Analyte Measurement Devices, Apparatuses and Systems

Figure 2:
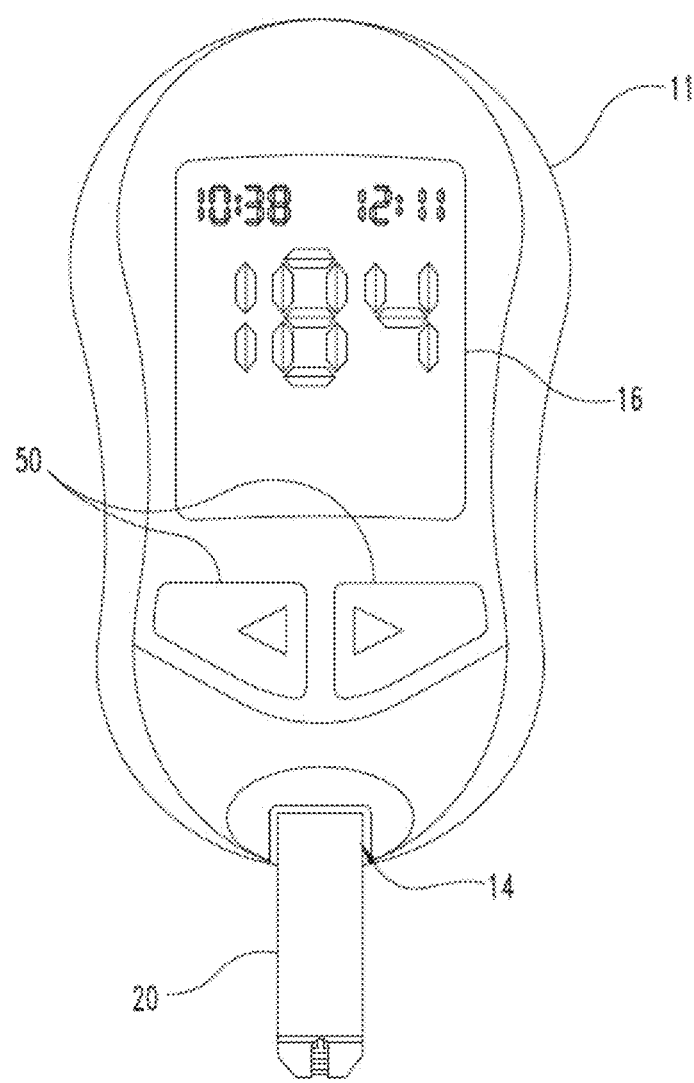
FIG. 2 shows an exemplary analyte measurement system including a meter and a biosensor.

Prior to, and in connection with, describing the inventive measurement methods, FIG. 2 shows an exemplary analyte measurement system including a device such as a test meter 11 operatively coupled with an electrochemical biosensor 20 (also known as a test element). Meter 11 and biosensor 20 are operable to determine concentration of one or more analytes in a fluidic sample provided to the biosensor 20. In some instances, the sample may be a body fluid sample such as, for example, whole blood, plasma, serum, urine or saliva. In other instances, the fluidic sample may be another type of sample to be tested for the presence or concentration of one or more electrochemically reactive analyte(s) such as an aqueous environmental sample.

In FIG. 2, the biosensor 20 is a single use test strip removably inserted into a connection terminal 14 of meter 11. In some instances, biosensor 20 is configured as a blood glucose test element and includes features and functionalities for electrochemically measuring glucose. In other instances, biosensor 20 is configured to electrochemically measure one or more other analytes such as, for example, amino acids, antibodies, bacteria, carbohydrates, drugs, lipids, markers, nucleic acids, peptides, proteins, toxins, viruses, and other analytes.

Meter 11 includes an electronic display 16 that is used to display various types of information to the user including analyte concentration(s) or other test results, and user interface 50 for receiving user input. Meter 11 further includes a microcontroller and associated test signal generating and measuring circuitry (not shown) that are operable to generate a test signal, to apply the signal to the biosensor 20, and to measure one or more responses of the biosensor 20 to the test signal. In some instances, meter 11 can be configured as a blood glucose measurement meter and includes features and functionalities of the ACCU-CHEK® AVIVA® meter as described in the booklet "Accu-Chek® Aviva Blood Glucose Meter Owner's Booklet" (2007), portions of which are disclosed in U.S. Pat. No. 6,645,368. In other instances, meter 11 can be configured to electrochemically measure one or more other analytes such as, for example, amino acids, antibodies, bacteria, carbohydrates, drugs, lipids, markers, nucleic acids, proteins, peptides, toxins, viruses, and other analytes. Additional details regarding exemplary meters configured for use with electrochemical measurement methods are disclosed in, for example, U.S. Pat. Nos. 4,720,372; 4,963,814; 4,999,582; 4,999,632; 5,243,516; 5,282,950; 5,366,609; 5,371,687; 5,379,214; 5,405,511; 5,438,271; 5,594,906; 6,134,504; 6,144,922; 6,413,213; 6,425,863; 6,635,167; 6,645,368; 6,787,109; 6,927,749; 6,945,955; 7,208,119; 7,291,107; 7,347,973; 7,569,126; 7,601,299; 7,638,095 and 8,431,408.

One of skill in the art understands that the measurement methods described herein can be used in other measurement devices, apparatuses, systems and environments such as, for example, hospital test systems, laboratory test systems and others.

It shall be understood that the biosensor and meter can include additional and/or alternate attributes and features in addition to or instead of those shown in FIG. 2. For example, the biosensor can be in the form of a single use, disposable electrochemical test strip having a substantially rectangular shape. It shall be appreciated that the biosensors can include different forms such as, for example, test strips of different configurations, dimensions or shapes, non-strip test elements, disposable test elements, reusable test elements, micro-arrays, lab-on-chip devices, bio-chips, bio-discs, bio-cds or other test elements. In some instances, the biosensor can include additional electrodes and reagents such as, for example, a dual assay biosensor for detecting glucose and ketones. See, e.g., U.S. patent application Ser. Nos. 13/667,057 and 13/667,154. Additional details regarding exemplary biosensors configured for use with electrochemical measurement methods are disclosed in, for example, U.S. Pat. Nos. 5,694,932; 5,762,770; 5,948,695; 5,975,153; 5,997,817; 6,001,239; 6,025,203; 6,162,639; 6,245,215; 6,271,045; 6,319,719; 6,406,672; 6,413,395; 6,428,664; 6,447,657; 6,451,264; 6,455,324; 6,488,828; 6,506,575; 6,540,890; 6,562,210; 6,582,573; 6,592,815; 6,627,057; 6,638,772; 6,755,949; 6,767,440; 6,780,296; 6,780,651; 6,814,843; 6,814,844; 6,858,433; 6,866,758; 7,008,799; 7,063,774; 7,238,534; 7,473,398; 7,476,827; 7,479,211; 7,510,643; 7,727,467; 7,780,827; 7,820,451; 7,867,369; 7,892,849; 8,180,423; 8,298,401; 8,329,026, as well as RE42560, RE42924 and RE42953.

Measurement Methods

Measurement Methods Having an Antioxidant Failsafe: As noted above, the measurement methods described herein are based upon an inventive concept that includes using information derived from a test sequence having at least one DC block, where the block is designed to provide specific information about a status of a redox mediator during the electrochemical analysis. In particular, the information relates to amounts of $M_{ox}$ and $M_{red}$ (or ratios thereof), as well as a status of $M_{ox}$ and $M_{red}$ features, during the electrochemical analysis.

Figure 3A:
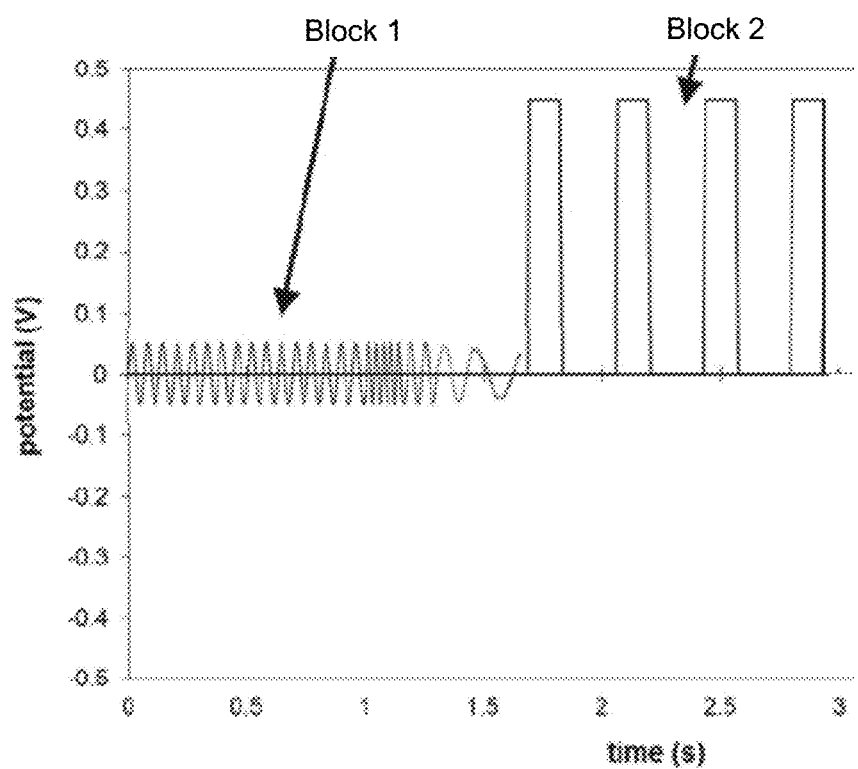
FIG. 3A-B show exemplary test sequences having two (2) blocks that may be employed by an analyte measurement device, apparatus or system, where
Figure 3B:
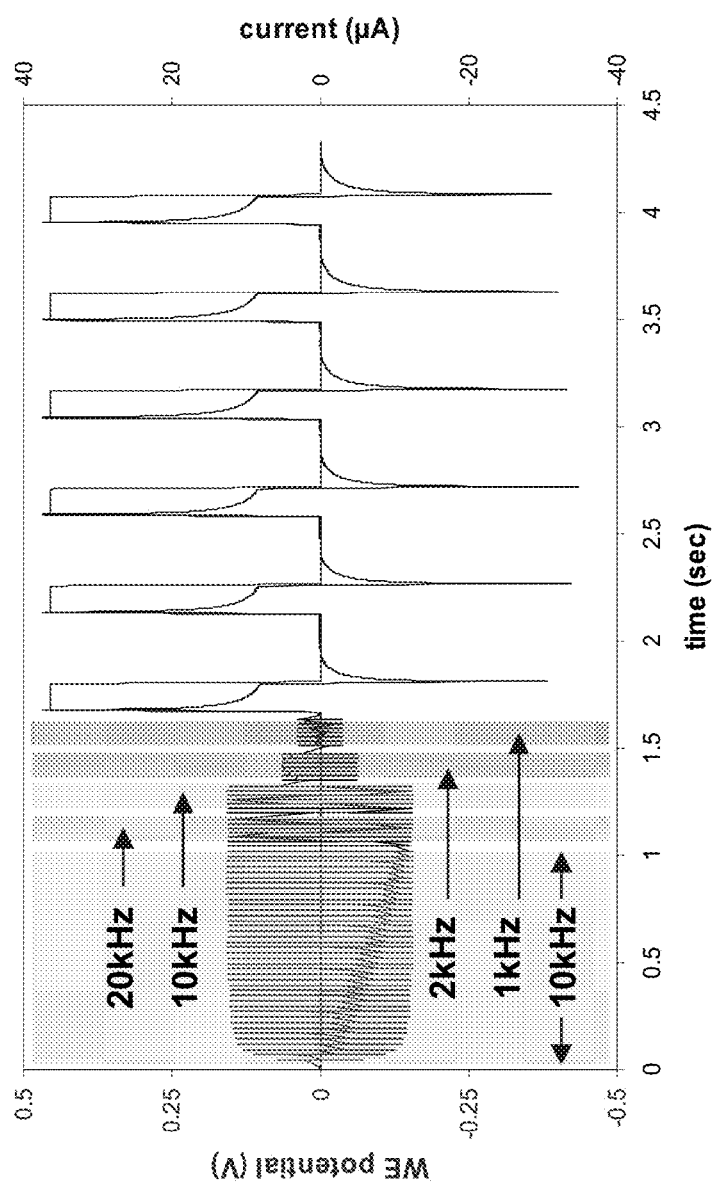

The methods generally include applying to a fluidic sample, such as a body fluid, a test sequence having at least one DC block and measuring the DC current responses. Alternatively, the methods can include applying a test sequence also having a block of low-amplitude AC segments in connection with at least one DC block and measuring the AC and DC current responses. FIGS. 3A-B show exemplary test sequences that may be used in connection with SMBGs and other test systems. The test sequence can include two blocks, where, for example, one block includes an AC block followed by a controlled, DC block.

When part of the test sequence, the AC block can include a plurality of AC segments such as, for example, from about 2 segments to about 10 segments, from about 3 segments to about 9 segments, from about 4 segments to about 8 segments, from about 5 segments to about 7 segments, or about 6 segments. In other instances, the AC block can include about 2 segments, about 3 segments, about 4 segments, about 5 segments, about 6 segments, about 7 segments, about 8 segments, about 9 segments, or about 10 segments. In still other instances, the AC block can have more than 10 segments, that is, about 15 segments, about 20 segments, or about 25 segments. In yet other instances, the AC block can include 1 segment, where the segment has multiple low-frequency AC signals applied simultaneously.

One of skill in the art understands that the number of AC segments will be limited by the complexity of the response, the associated frequency range and time available to perform the measurements. Higher frequencies generally require high bandwidth electronics and faster sampling, whereas lower frequencies take longer and are typically noisier. The maximum number of segments therefore will be a compromise of these parameters, choosing the minimum count and frequency span needed to discriminate the sample and environmental and/or interferents of interest.

As used herein, "about" means within a statistically meaningful range of a value or values such as a stated concentration, length, molecular weight, pH, potential, time frame, temperature, voltage or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The frequency of each signal in each segment of the AC block can be from about 1 kHz to about 20 kHz, from about 2 kHz to about 19 kHz, from about 3 kHz to about 18 kHz, from about 4 kHz to about 17 kHz, from about 5 kHz to about 16 kHz, from about 6 kHz to about 15 kHz, from about 7 kHz to about 14 kHz, from about 8 kHz to about 13 kHz, from about 9 kHz to about 12 kHz or from about 10 kHz to about 11 kHz. In other instances, the frequency of each segment in the AC block can be about 1 kHz, about 2 kHz, about 3 kHz, about 4 kHz, about 5 kHz, about 6 kHz, about 7 kHz, about 8 kHz, about 9 kHz, about 10 kHz, about 11 kHz, about 12 kHz, about 13 kHz, about 14 kHz, about 15 kHz, about 16 kHz, about 17 kHz, about 18 kHz, about 19 kHz, or about 20 kHz. In still other instances, the frequency of each signal in each segment of the AC block can be more than 20 kHz, that is, about 30 kHz, about 40 kHz, or about 50 kHz. In some instances, one or more of the segments can have the same frequency, whereas in other instances each segment has a distinct frequency from the other segments. Four frequencies, however, generally is adequate. The exact frequencies employed can be readily generated by simple integer division of a measurement system clock's maximum frequency.

A maximum frequency limit for a signal in a segment of the AC block, however, can be up to about 100 kHz for an inexpensive, battery-powered handheld instrument. Beyond that, the increasing demands on analog bandwidth, sampling rate, storage and processing speed quickly add up, while the imaginary portion of a typical biosensor response becomes increasingly smaller with frequency. Lower frequencies have longer periods and take longer times to sample with comparable accuracy.

The AC block typically includes at least two different low-amplitude signals. For example, the AC block can include two (2) segments at two (2) frequencies such as, for example, about 10 kHz or about 20 kHz followed by about 1 kHz or about 2 kHz. In other instances, the AC block includes a plurality of low-amplitude signals. For example, the AC block can have five (5) segments at four (4) frequencies such as, for example, about 10 kHz, about 20 kHz, about 10 kHz, about 2 kHz and about 1 kHz. Alternatively, the AC block can have four (4) segments at four (4) frequencies such as, for example, about 20 kHz, about 10 kHz, about 2 kHz and about 1 kHz. Alternatively, the AC block can have four (4) frequencies applied simultaneously at about 10 kHz, about 20 kHz, about 10 kHz, about 2 kHz and about 1 kHz. Alternately still, the AC block can have a multi-frequency excitation waveform that simultaneously applies the desired low-amplitude AC signals. The AC frequencies may be applied sequentially, or combined and applied simultaneously and analyzed via Fourier Transform.

The AC block can be applied for about 500 msec to about 1.5 sec, about 600 msec to about 1.25 sec, about 700 msec to about 1 sec, or about 800 msec to about 900 msec. Alternatively, the AC block can be applied for about 500 msec, about 600 msec, about 700 msec, about 800 msec, about 900 msec, about 1 sec, about 1.25 sec or about 1.5 sec. In particular, the AC block is applied for about 100 msec to about 300 msec.

One of skill in the art, however, understands that the number, frequency, duration and order of the AC segments can be varied.

AC current response information can be obtained at any time during a test sequence. Impedance results at lower frequencies may be influenced by analyte concentration if obtained after an electrochemical cell is DC polarized. In some instances, a series of AC current response measurements can be obtained early in the test sequence. Measurements taken shortly after a fluidic sample is applied to a biosensor will be influenced by diffusion, temperature and reagent solubility. In other instances, the AC response current measurements can be obtained at a sufficient time after an adequate sample has been applied to allow the response to stabilize, and avoid the transient response in the first second. Likewise, response current measurements can be made at one or more frequencies. Due to their capacitive nature, multiple AC measurements separated by a frequency octave or decade may offer different sensitivities or easier manipulation.

Additional details regarding exemplary AC blocks in electrochemical measurement methods are disclosed in, for example, U.S. Pat. Nos. 7,338,639; 7,390,667; 7,407,811; 7,417,811; 7,452,457; 7,488,601; 7,494,816; 7,597,793; 7,638,033; 7,751,864; 7,977,112; 7,981,363; 8,148,164; 8,298,828; 8,377,707 and 8,420,404.

The inventive concept is based upon a DC block in which a DC potential profile is applied and is used for detecting an antioxidant such as ascorbate and an indication of general chemistry health of the electrochemical system including the sample.

The DC block (e.g., as described in greater detail below in connection with FIGS. 8-10) generates unique response information resulting from applying a SRBP waveform. In theory, any DC excitation with sufficient potential to cause an electrochemical reaction of the redox mediator on the electrodes will produce a current response that can be used to quantitatively measure an analyte such as glucose. This current response also will be impacted by changing Hct and temperature levels. This research assessed the value of SRBP waveforms to determine whether additional, unique information could be obtained and used to improve analyte measurement system performance and/or capabilities, in much the same way that the use of recovery pulse information in combination with excitation pulse information can be utilized to improve performance.

The SRBP waveform can include a plurality of intervals such as, for example, from about 2 intervals to about 10 intervals, from about 3 intervals to about 9 intervals, from about 4 intervals to about 8 intervals, from about 5 intervals to about 7 intervals, or about 6 intervals. In other instances, the SRBP waveform can include about 1 interval, about 2 intervals, about 3 intervals, about 4 intervals, about 5 intervals, about 6 intervals, about 7 intervals, about 8 intervals, about 9 intervals, or about 10 intervals. In still other instances, the SRBP waveform can have more than 10 intervals, that is, about 15 intervals, about 20 intervals, or about 25 intervals. The number of SRBP waveform intervals, however, typically is limited by the available time for the test sequence.

The SRBP waveform intervals can be at a potential that alternates or cycles between a positive potential and a negative potential (or vice versa). For example, the potential can alternate from about −450 mV to about +450 mV, from about −425 mV to about +425 mV, from about −400 mV to about +400 mV, from about −375 mV to about +375 mV, from about −350 mV to about +350 mV, from about −325 mV to about +325 mV, from about −300 mV to about +300 mV, from about −275 mV to about +275 mV, from about −250 mV to about +250 mV, from about −225 mV to about +225 mV, from about −200 mV to about +200 mV, from about −175 mV to about +175 mV, from about −150 mV to about +150 mV, from about −125 mV to about +125 mV, from about −100 mV to about +100 mV, from about −75 mV to about +75 mV, or from about −50 my to about +50 mV. In some instances, one or more of the successive cycles can have the same potential, whereas in other instances the successive cycles have a distinct potential from the other segments.

Regardless of the number, each SRBP waveform interval can be applied for about 100 msec to about 5 sec, from about 200 msec to about 4 sec, from about 300 msec to about 3 sec, from about 400 msec to about 2 sec, from about 500 msec to about 1 sec, from about 600 msec to about 900 msec, or from about 700 msec to about 800 msec. Alternatively, each SRBP waveform interval can be applied for about 100 msec, about 150 msec, about 200 msec, about 250 msec, about 300 msec, about 350 msec, about 400 msec, about 450 msec, about 500 msec, about 550 msec, about 600 msec, about 650 msec, about 700 msec, about 750 msec, about 800 msec, about 850 msec, about 900 msec, about 950 msec, about 1 sec, about 1.5 sec, about 2 sec, about 2.5 sec, about 3 sec, about 3.5 sec, about 4 sec, about 4.5 sec, or about 5 sec. In particular, each SRBP waveform interval at about −450 mV can be applied for about 100 msec to about 200 msec, and each SRBP waveform interval at about +450 mV can be applied for about 100 msec to about 200 msec. Alternatively still, each SRBP waveform interval can be applied for less than about 100 msec or more than about 5 sec.

In some instances, the SRBP waveform intervals can have the same ramp rates. In other instances, some SRBP waveform intervals can have the same ramp rate and other SRBP waveform intervals can have a different ramp rate. In still other instances, each SRBP waveform interval has its own ramp rate. For example, the ramp rate can be from about 0.5 mV/msec to ≤45 mV/msec. Alternatively, the ramp rate of each interval can be from about 1 mV/msec to about 40 mV/msec, from about 2 mV/msec to about 30 mV/msec, from about 3 mV/msec to about 20 mV/msec, from about 4 mV/msec to about 19 mV/msec, from about 5 mV/msec to about 18 mV/msec, from about 6 mV/msec to about 17 mV/msec, from about 7 mV/msec to about 16 mV/msec, from about 8 mV/msec to about 15 mV/msec, from about 9 mV/msec to about 14 mV/msec, or from about 10 mV/msec to about 13 mV/msec, or about 11 mV/msec to about 12 mV/msec. Alternatively, the ramp rate of each intervals can be about 0.5 mV/msec, 1 mV/msec, about 2 mV/msec, about 3 mV/msec, about 4 mV/msec, about 5 mV/msec, about 6 mV/msec, about 7 mV/msec, about 8 mV/msec, about 9 mV/msec, about 10 mV/msec, about 11 mV/msec, about 12 mV/msec, about 13 mV/msec, about 14 mV/msec, about 15 mV/msec, about 16 mV/msec, about 17 mV/msec, about 18 mV/msec, about 19 mV/msec, about 20 mV/msec, about 25 mV/msec, about 30 mV/msec, about 35 mV/msec, about 40 mV/msec, or about 45 mV/msec. In particular, the ramp rate is between about 3 mV/msec and about 9 mV/msec, such as about 5.1 mV/msec or about 7.15 mV/msec.

In some instances, the SRBP waveform can be a triangular waveform, trapezoidal waveform, sinusoidal waveform or combinations thereof.

With respect to the second, or alternative, DC block that can be included in the test sequence, one example includes a constantly applied potential difference that alternates between about 0 mV and a predetermined positive potential difference, or other slowly time-varying potential difference that can be analyzed by traditional DC electrochemical methods. One of skill in the art, however, understands that the range for the applied potential difference can, and will, vary depending upon the analyte and reagent chemistry used.

This DC block can include a plurality of pulses such as, for example, from about 2 pulses to about 10 pulses, from about 3 pulses to about 9 pulses, from about 4 pulses to about 8 pulses, from about 5 pulses to about 7 pulses, or about 6 pulses. In other instances, the DC block can include about 1 pulse, about 2 pulses, about 3 pulses, about 4 pulses, about 5 pulses, about 6 pulses, about 7 pulses, about 8 pulses, about 9 pulses, or about 10 pulses. In still other instances, the DC block can have more than 10 pulses, that is, about 15 pulses, about 20 pulses, or about 25 pulses. As used herein, "pulse" means at least one excitation and/or one recovery potential period. The number of pulses, however, typically is limited by the available time for the test sequence. Shorter durations probe further from the electrode surface, and increase sensitivity to reagent thickness and diffusion modifiers.

The potential of each pulse in the DC block can be from about 0 mV to about 450 mV, from about 10 mV to about 425 mV, from about 15 mV to about 400 mV, from about 20 mV to about 375 mV, from about 25 mV to about 350 mV, from about 30 mV to about 325 mV, from about 35 mV to about 300 mV, from about 40 mV to about 275 mV, from about 45 mV to about 250 mV, from about 50 mV to about 225 mV, from about 75 mV to about 200 mV, from about 100 mV to about 175 mV, or from about 125 mV to about 150 mV. In other instances, the potential of each pulse in the DC block can be about 1 mV, about 10 mV, about 15 mV, about 20 mV, about 25 mV, about 30 mV, about 35 mV, about 40 mV, about 45 mV, about 50 mV, about 60 mV, about 70 mV, about 80 mV, about 90 mV, about 100 mV, about 110 mV, about 120 mV, about 130 mV, about 140 mV, about 150 mV, about 160 mV, about 170 mV, about 180 mV, about 190 mV, about 200 mV, about 210 mV, about 220 mV, about 230 mV, about 240 mV, about 250 mV, about 260 mV, about 270 mV, about 280 mV, about 290 mV, about 300 mV, about 310 mV, about 320 mV, about 330 mV, about 340 mV, about 350 mV, about 360 mV, about 370 mV, about 380 mV, about 390 mV, about 400 mV, about 410 mV, about 420 mV, about 430 mV, about 440 mV, or about 450 mV. In still other instances, the potential of each pulse of the DC block can be more than 450 mV, that is, about 475 mV, about 500 mV, about 525 mV, about 550 mV, about 575 mV, about 600 mV kHz, about 625 mV, about 650 mV, about 675 mV, about 700 mV, about 725 mV, or about 750 mV. In still other instances, the excitation pulse potential can be greater-than, less-than or equal to about +450 mV. In some instances, one or more of the pulses can have the same potential, whereas in other instances each pulse has a distinct potential from the other pulses.

As noted above, the applied DC potential can be fixed at about 0 mV between excitation pulses to provide a recovery pulse, thus making it a generally continuous, unipolar excitation waveform. This is in contrast to a test signal sequence from known methods that prescribe the use of an open circuit between positive DC pulses, thereby excluding the possibility of collecting and analyzing the current between positive pulses.

Regardless of the number, each DC pulse can be applied for about 50 msec to about 500 msec, about 60 msec to about 450 msec, about 70 msec to about 400 msec, about 80 msec to about 350 msec, about 90 msec to about 300 msec, about 100 msec to about 250 msec, about 150 msec to about 200 msec, or about 175 msec. Alternatively, each pulse can be applied for about 50 msec, about 60 msec, about 70 msec, about 80 msec, about 90 msec, about 100 msec, about 125 msec, about 150 msec, about 175 msec, about 200 msec, about 225 msec, about 250 msec, about 275 msec, about 300 msec, about 325 msec, about 350 msec, about 375 msec, about 400 msec, about 425 msec, about 450 msec, about 475 msec or about 500 msec. In particular, each DC pulse at about +450 mV can be applied for about 250 msec, and each DC pulse at about 0 mV can be applied for about 500 msec. Alternatively still, each pulse can be applied for less than about 50 msec or more than about 500 msec. The duration should be long enough or the onset soft enough to avoid charging currents. Regardless, the pulse duration should be applied long enough to enable reasonable 50/60 Hz noise rejection. Moreover, the time between pulses is ideally long enough to allow the electrochemical cell to discharge and return close to its pre-pulse state. Furthermore, the operating potential will depend upon the mediator and measurement system. The examples herein demonstrate proof-of-principal with NA-derived redox mediator.

Generally, the ramp rate of each pulse is selected to provide about 50% or greater reduction in peak current relative to the peak current provided by a nearly ideal potential transition. In some instances, each pulse can have the same ramp rate. In other instances, some pulses can have the same ramp rate and other pulses can have a different ramp rate. In still other instances, each pulse has its own ramp rate. For example, effective ramp rates can be from about 5 mV/msec to about 75 mV/msec or from about 10 mV/msec to about 50 mV/msec, 15 mV/msec to about 25 mV/msec, or about 20 mV/msec. Alternatively, the ramp rate can be about 5 mV/msec, about 10 mV/msec, about 15 mV/msec, about 20 mV/msec, about 25 mV/msec, about 30 mV/msec, about 35 mV/msec, about 40 mV/msec, about 45 mV/msec, about 50 mV/msec, about 55 mV/msec, about 60 mV/msec, about 65 mV/msec, about 70 mV/msec, or about 75 mV/msec. In particular, the ramp rate can be from about 40 mV/msec to about 50 mV/msec.

With this DC block, a closed circuit, 0 mV DC potential is applied to provide a recovery pulse, thus making it a continuous excitation potential profile. This is in contrast to the use of an open circuit between non-zero DC pulses. The use of a recovery pulse allows the collection and analysis of response currents during the duration of the recovery pulses in addition to the current response information during non-zero pulses. The recovery pulse, can be viewed as an adequately long recovery period in which at least part of the electrochemical reaction with an analyte such as glucose is turned off, thereby allowing the system to return to a common starting point before subsequent interrogation with another non-zero pulse.

Like the AC block, one of skill in the art understands that the number, potential, duration and order of the pulses in this DC block can be varied.

In some instances, the AC block can be applied before the at least one DC block, after the at least one DC block, or interspersed therewith. Alternatively, the AC block is applied before the at least one DC block. In some instances, the test sequence includes a single DC block, whereas in other instances the test sequence includes two or more DC blocks.

In the methods, the AC and/or DC response current information can be obtained (i.e., measured or recorded) at about 2,000/sec to about 200,000/sec, at about 3,000/sec to about 190,000/sec, at about 4,000/sec to about 180,000/sec, at about 5,000/sec to about 170,000, at about 6,000/sec to about 160,000/sec, at about 7,000/sec to about 150,000/sec, at about 8,000/sec to about 140,000/sec, at about 9,000/sec to about 130,000/sec, at about 10,000/sec to about 120,000/sec, at about 15,000/sec to about 110,000/sec, at about 20,000/sec to about 100,000/sec, at about 30,000/sec to about 90,000/sec, at about 40,000/sec to about 80,000/sec, at about 50,000/sec to about 70,000/sec, or at about 60,000/sec. In some instances, the AC and/or DC response current information can be obtained at about 100/sec to about 200/sec, at about 200/sec to about 300/sec, at about 300/sec to about 400/sec, at about 400/sec to about 500/sec, at about 500/sec to about 600/sec, at about 600/sec to about 700/sec, at about 700/sec to about 800/sec, at about 800/sec to about 900/sec, at about 1,000/sec to about 1,500/sec, at about 1,500/sec to about 2,000/sec, at about 2,000/sec to about 2,500/sec, at about 2,500/sec to about 3,000/sec, at about 3,000/sec to about 3,500/sec, at about 3,500/sec to about 4,000/sec, at about 4,000/sec to about 4,500/sec, at about 4,500/sec to about 5,000/sec, at about 5,000/sec to about 5,500/sec, at about 5,500/sec to about 6,000/sec, at about 6,000/sec to about 6,500/sec, at about 6,500 to about 7,000/sec, at about 7,000/sec to about 7,500/sec, at about 7,500/sec to about 8,000/sec, at about 8,000/sec to about 8,500/sec, at about 8,500 to about 9,000/sec, at about 9,000/sec to about 9,500/sec, at about 9,500/sec to about 10,000/sec, at about 10,000/sec to about 20,000/sec, at about 20,000/sec to about 30,000/sec, at about 30,000/sec to about 40,000/sec, at about 40,000/sec to about 50,000/sec, at about 50,000/sec to about 60,000/sec, at about 60,000/sec to about 70,000/sec, at about 70,000/sec to about 80,000/sec, at about 80,000/sec to about 90,000/sec, at about 90,000/sec to about 100,000/sec, at about 100,000/sec to about 110,000/sec to about 120,000/sec, at about 120,000/sec to about 130,000/sec, at about 130,000/sec to about 140,000/sec, at about 140,000/sec to about 150,000/sec, at about 150,000/sec to about 160,000/sec, at about 160,000/sec to about 170,000/sec, at about 170,000/sec to about 180,000/sec, at about 180,000/sec to about 190,000/sec, or at about 200,000/sec. In other instances, the AC and/or DC response current information can be obtained up to about 100/sec, about 200/sec, about 300/sec, about 400/sec, about 500/sec, 600/sec, about 700/sec, about 800/sec, about 900/sec, about 1,000/sec, about 1,250/sec, about 1,500/sec, about 1,750/sec, about 2,000/sec, about 2,225/sec, about 2,500/sec, about 2,750/sec, about 3,000/sec, about 3,250/sec, about 3,500/sec, about 3,750/sec, about 4,000/sec, about 4,250/sec, about 4,500/sec, about 4,750/sec, about 5,000/sec, about 5,250/sec, about 5,500/sec, about 5,750/sec, about 6,000/sec, about 6,250/sec, about 6,500, about 7,000/sec, about 7,250/sec, about 7,500/sec, about 7,750/sec, about 8,000/sec, about 8,250/sec, about 8,500/sec, about 8,750, about 9,000/sec, about 9,250/sec, about 9,500/sec, about 9,750/sec, about 10,000/sec, about 15,000/sec, about 20,000/sec, about 25,000/sec, about 30,000/sec, about 35,000/sec, about 40,000/sec, about 45,000/sec, about 50,000/sec, about 55,000/sec, about 60,000/sec, about 65,000/sec, about 70,000/sec, about 75,000/sec, about 80,000/sec, about 85,000/sec, about 90,000/sec, about 95,000/sec, about 100,000/sec, about 105,000/sec, about 110,000/sec, about 115,000/sec, about 120,000/sec, about 125,000/sec, about 130,000/sec, about 135,000/sec, about 140,000/sec, about 145,000/sec, about 150,000/sec, about 155,000/sec, about 160,000/sec, about 165,000/sec, about 170,000/sec, about 175,000/sec, about 180,000/sec, about 185,000/sec, about 190,000/sec, about 195,000/sec or at about 200,000/sec. In yet other instances, the AC and/or DC response current information can be obtained at more than 200,000/sec.

AC and/or DC current response information can be collected from the test sequence and includes current responses to the AC and DC blocks. In some instances, the current response information can be collected at an A/D sampling rate for DC and AC measurements to simplify the system design, including a single shared signal path for AC and DC measurements. Common digital audio sampling rates range include, but are not limited to, from about 44.1 kHz to about 192 kHz. A/D converters in this range are readily available from variety of commercial semiconductor suppliers.

Current response information (e.g., duration, shape and/or magnitude) to the AC block may be used for determining admittance and phase values or other complex parameters as described in further detail below. Current response information to this DC block can be used for measuring an analyte such as glucose or another analyte subject to analysis through oxidation/reduction techniques. In addition, the current response information also can be used to examine for Hct and temperature effects on the analyte concentration.

In view of the foregoing, an exemplary test sequence can include: (1) a DC block of short-duration (e.g., about 50-500 msec) about +450-mV segments separated by similarly short-duration (e.g., about 50-500 msec) segments during which a closed circuit about −450-mV potential is applied. An alternative exemplary test sequence can include: (1) an AC block of a plurality of low-amplitude AC segments at different frequencies; (2) a DC block of short-duration about +450-mV segments separated by similarly short-duration segments during which a closed circuit about −450-mV potential is applied. A further exemplary test sequence can include: (1) an AC block of a plurality of low-amplitude AC segments at different frequencies; (2) a DC block of short-duration about +450-mV pulses separated by similarly short-duration segments during which a closed circuit about 0-mV recovery potential is applied; and (3) a DC block of short-duration (e.g., about 50-500 msec) about +450-mV pulses separated by similarly short-duration (e.g., about 50-500 msec) recovery pulses during which a closed circuit about −450-mV recovery potential is applied.

Once the response information is collected, the methods then include providing a qualitative or quantitative antioxidant failsafe that distinguishes between samples containing antioxidant levels with less than a predetermined concentration from samples that have antioxidant levels that are greater than the predtermined concentration. The failsafe functionality can be used with an electrochemical system that can provide impedance characteristics of the cell and pulsed amperometric measurements that are unipolar or bipolar. It also can be used in electrochemical systems where the electrochemical cell is simultaneously excited with broad-band frequencies and DC pulsing of unipolar or bipolar form. The failsafe function may be utilized in connection with test systems configured to determine concentration of a number of different analytes. In some instances, the failsafe may be used in conjunction with a glucose test system such as an SMBG system. If the failsafe identifies the sample to have a safe antioxidant level at which the calculated glucose concentration would be reliable, the user may be presented with the calculated glucose level. Otherwise, the user may be presented with an error code indicating that the antioxidant level or other interferent exceeds a predetermined threshold at which a reliable glucose concentration can be delivered. For example, the predetermined threshold for ascorbate in a sample can be about 3 mg/dL or higher, about 4 mg/dL or higher, about 5 mg/dL or higher, about 6 mg/dL or higher, about 7 mg/dL or higher, about 8 mg/dL or higher, about 9 mg/dL or higher or about 10 mg/dL or higher.

To determine the excitation potential for a given redox mediator, one may plot current measured a fixed time after a selected working electrode/counter-electrode (WE-CE) potential step is applied (e.g., 3.5 sec). In any case, one of skill in the art would strive to operate comfortably on a current-potential plateau. Higher potentials, however, are not always better as they can invite other (i.e., interfering) reactions that may undesirably contribute to the analyte measurement of interest.

Figure 4A:
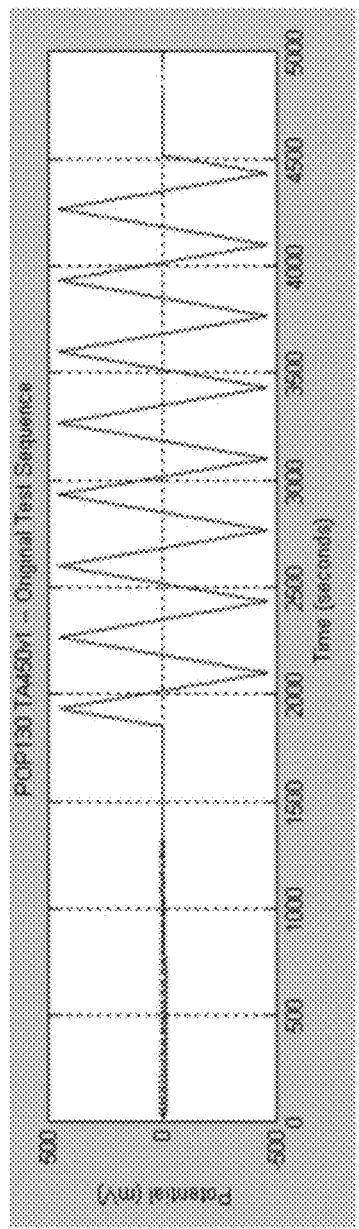
FIG. 4A shows an exemplary test sequence having an AC excitation frequency followed by a DC block of a SRBP triangular waveform.

FIG. 4A shows an exemplary SRBP waveform and its applied potential sequence. The test sequence shown includes an AC block similar to that discussed above and described in FIG. 3B but omitting the final 1 kHz frequency. Following the AC block, a controlled, triangular SRBP potential waveform can be applied. This potential profile defines a potentiodynamic experiment that is akin to cyclic voltammetry (CV). It should be noted, however, that this waveform is applied in biamperometric mode, without a reference electrode, which means it is not a CV measurement in the strict sense. The direction of potential scan was reversed each time the apparent applied potential reached +450 mV or −450 mV, respectively. Initial experiments were performed on a multi-channel, research-grade potentiostat, which sampled the current response at about 1000 Hz. This SRBP waveform was applied to a set of blood samples that spanned three (3) glucose concentrations (e.g., 40, 120 and 550 mg/dL), three (3) Hct levels (e.g., 25, 42 and 60%), and four (4) ascorbate concentrations (0, 5, 15 and 100 mg/dL). It shall be appreciated, however, that the methods disclosed herein are adaptable and thus equally applicable to clinical or over-the-counter (OTC) systems such as SMBG systems.

Figure 4B:
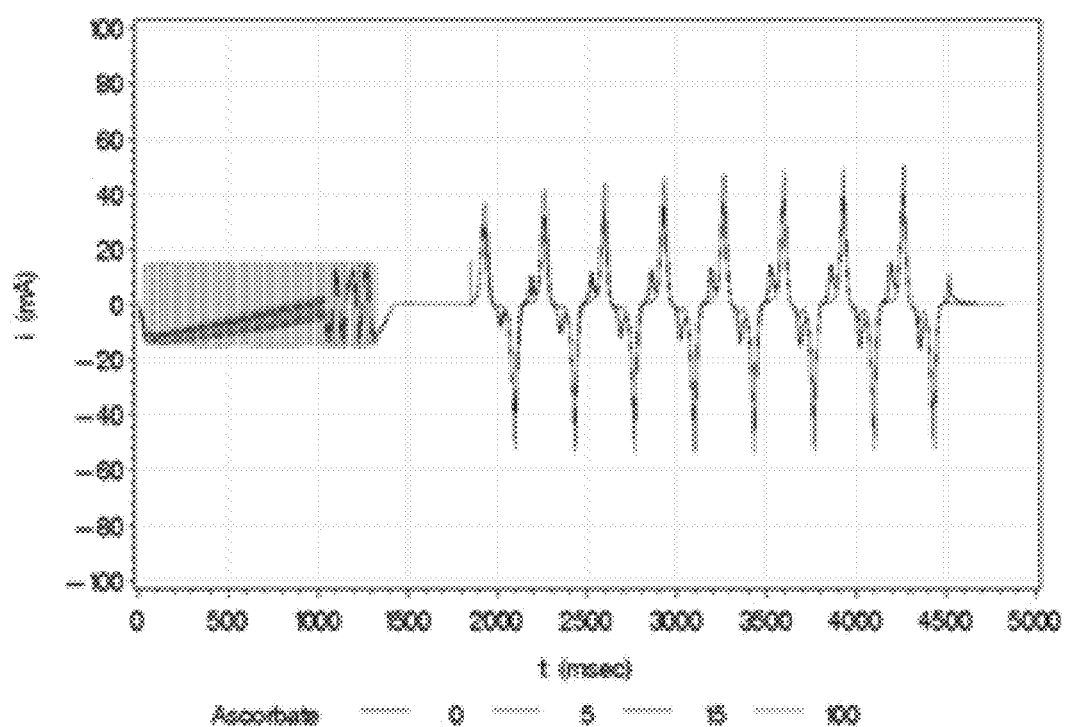
FIG. 4B shows current responses to the test sequence of FIG. 4A at four (4) different ascorbate levels for a blood sample containing 550 mg/dL glucose at 42% Hct.

FIG. 4B shows the current responses at each ascorbate level for the spiked blood sample with 550 mg/dL glucose and 42% Hct. The current response includes two distinct peaks for every +450-mV and −450-mV cycle after the first positive scan, respectively. Surprisingly, it was discovered that the smaller peak tracks ascorbate present in the sample in a quantitative manner.

FIGS. 5A-B show comparisons of two additional samples from the same data set. The upper left plot shows the CV (current in nA on the y-axis versus applied potential in mV on the x-axis) for the blood sample containing 550 mg/dL glucose at 25% Hct with no ascorbate. The upper right plot shows the current response (current in nA on the y-axis versus time in msec on the x-axis) for the same sample. The beginning cycle is shown in one color, and the last cycle is shown in another in each plot. In contrast, the lower right plot shows the CV for a blood sample also containing 550 mg/dL glucose at 25% Hct, but with ascorbate at 100 mg/dL. The lower right plot shows the current response versus time for the same sample.

Referring to the upper left plot, the feature located at an apparent applied potential of about ±50 mV was identified as reduction of QDI produced during the preceding scan, and the feature at +450 mV corresponds to oxidation of PDA. The assignments were confirmed using finite difference modeling of the chemical reactions and the electrochemical reactions. Although ascorbate is a strong antioxidant, it does not reduce the excess NA present in the reagent, but it readily reduces QDI formed during the measurement process, thereby forming additional PDA, which leads to the detection of additional current that was not produced by a reaction with glucose. Notice that the QDI feature is not discernable in the lower left voltammagram, which corresponds to high ascorbate. Comparing the CVs and/or the current responses for the two samples, a clear increase in the PDA feature is observed. Similar behaviors and signatures for QDI and PDA also can be seen at negative applied potentials.

Based upon the reaction described in connection with FIG. 1, it is important to understand that this method for detecting an antioxidant such as ascorbate is made possible in part because of the characteristics of reagent chemistry, in particular the characteristics of the redox mediator or redox mediator precursor. The choice of NA as a redox mediator is one example of a reagent chemistry that permits detection of an antioxidant such as ascorbate. However, any redox mediator that forms a species that can be easily reduced by an antioxidant could be used in a similar manner to implement the approaches described herein, provided that electrooxidation of the additional amount of mediator reduced by the antioxidant produces a response effect that is evident at potential excitations such as a DC block having a SRBP waveform, where glucose-based electrooxidation of the reduced mediator is not typically evident. This is not necessarily the case with some of the common redox mediators used for SMBGs, but is one effect of a mediator system based on a NA-derived redox mediator.

There are numerous interfering substances that can interfere with electrochemical detection of glucose or other analytes using a variety of different mechanisms. Of the common interferents tested during development of the measurement methods disclosed herein, ascorbate and glutathione both were observed to have this particular interaction with QDI. As such, it is believed that any interferent that readily reduces QDI will produce essentially a unique but similar signature (e.g., a decrease in the QDI feature, an increase in the QDI feature, a decrease in the PDA feature or an increase in the PDA feature). Even a lack of specificity among multiple interferents would not negate any of the advantages described above. If the FAD-GDH chemistry with NA-derived redox mediator is working properly, a sample (at given glucose, Hct and temperature levels) should produce a current response with a characteristic ratio of the QDI and PDA peak currents. If the QDI feature is not discernable, as seen in the lower right plot in FIG. 5B, this implies that there is something wrong with the chemistry system, either due to an excess of an antioxidant such as ascorbate or due to some other interferent. This situation will result in additional current arising from a different mechanism than just the reaction with glucose, thereby leading to an incorrect reading. Therefore, checking for the simple qualitative existence or absence of the QDI feature provides the basis for a failsafe. By measuring the QDI feature for each analyte measurement, one can safeguard users from ascorbate or other interferents that are reacting with the reagent, by not calculating an analyte concentration such as a bG value when one knows the chemistry is compromised. This redox mediator check can be performed mathematically in a variety of ways, including pattern recognition, discriminant analysis and simple heuristic comparisons using selected values from the current response.

Figure 6A:
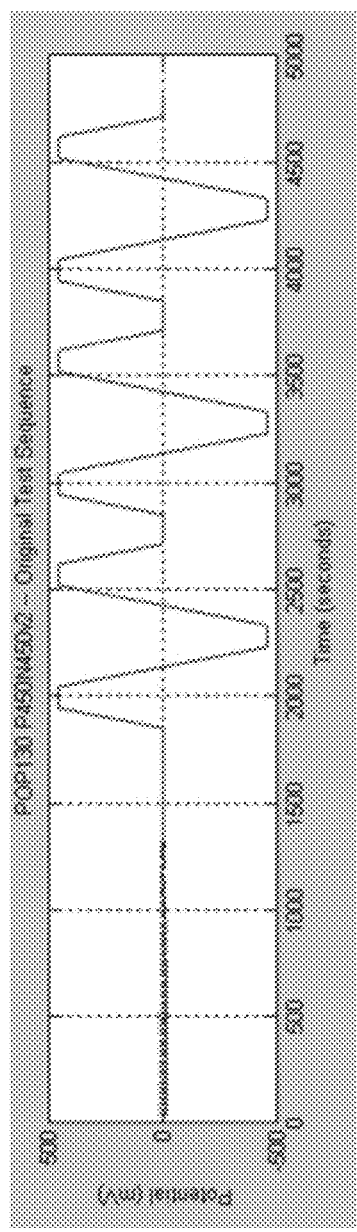
FIG. 6A shows another exemplary test sequence having an AC excitation at three (3) frequencies followed by a DC block of a SRBP trapezoidal waveform.
Figure 6B:
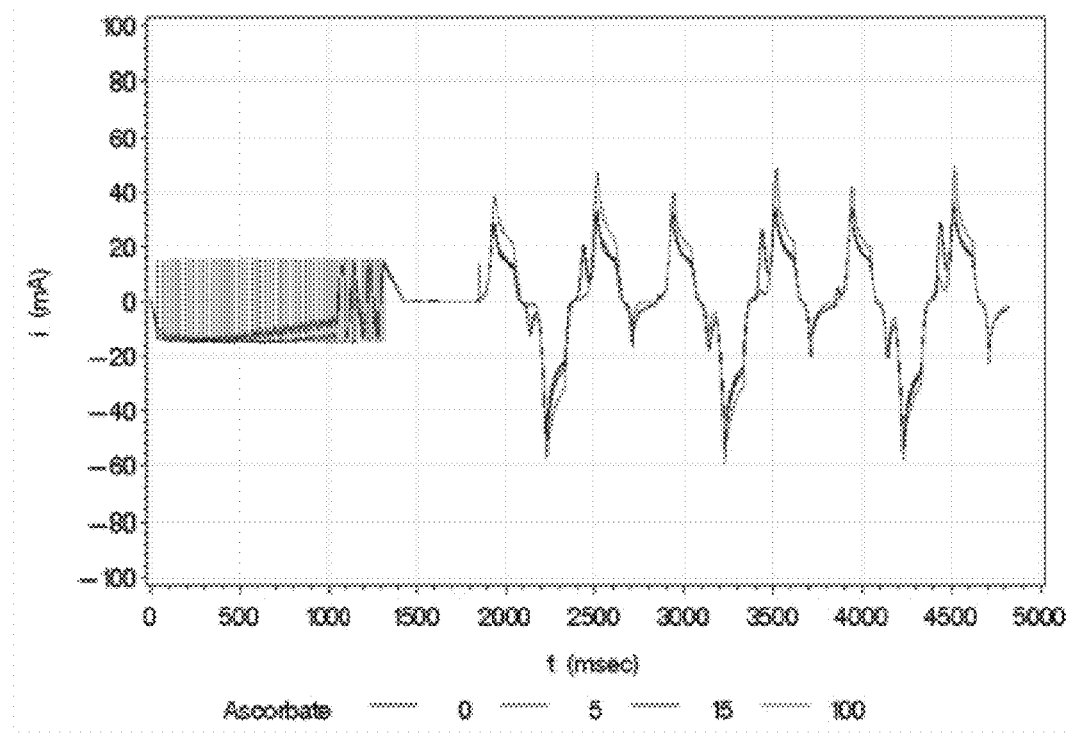
FIG. 6B shows current responses to the test sequence of FIG. 6A at four (4) different ascorbate levels for a blood sample containing 550 mg/dL glucose at 42% Hct.
Figure 7A:
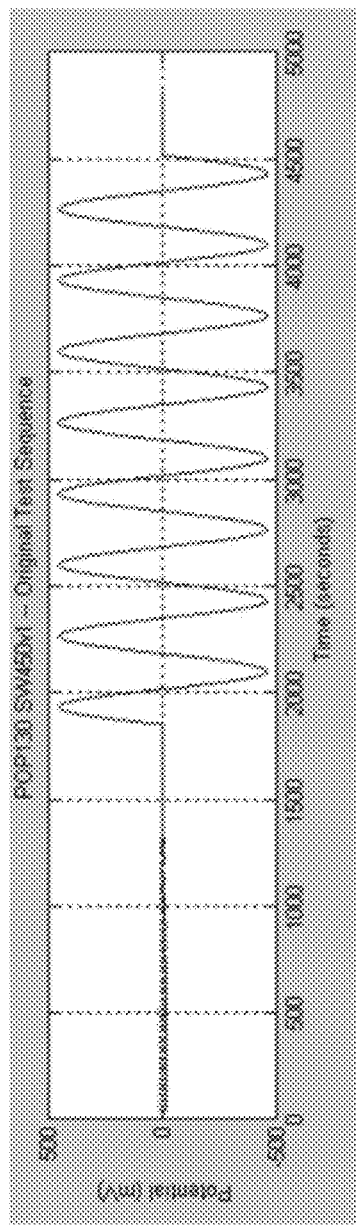
FIG. 7A shows another exemplary test sequence having an AC excitation at three (3) frequencies followed by a DC block of a SRBP sinusoidal waveform.
Figure 7B:
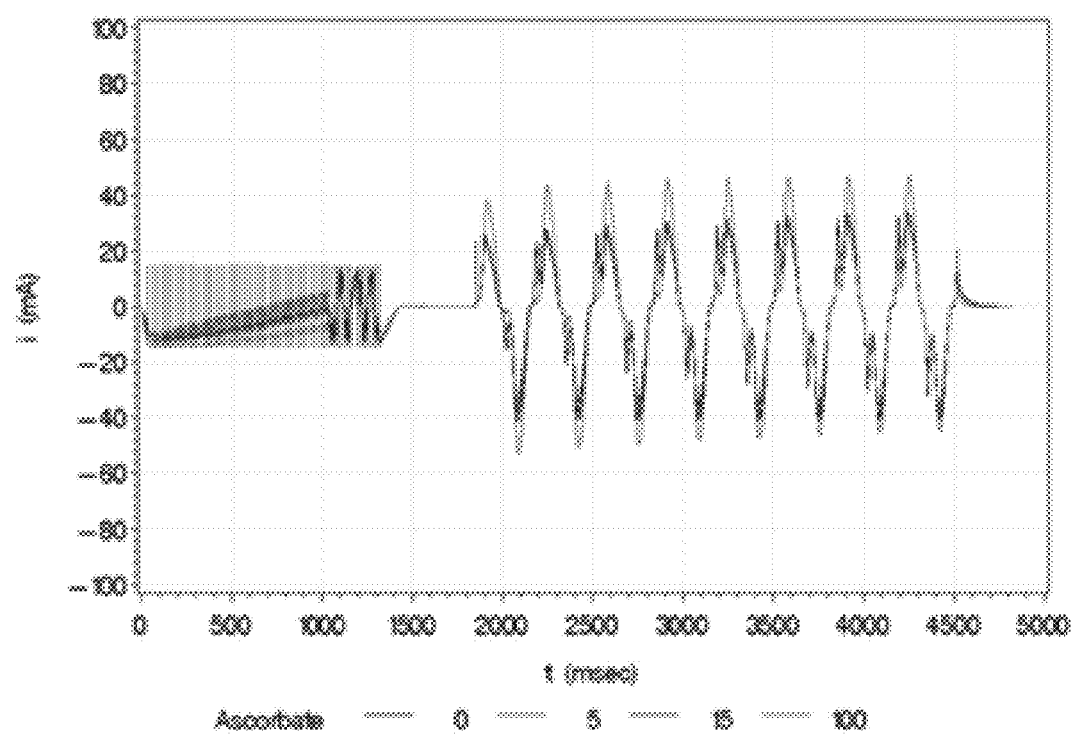
FIG. 7B shows current responses to the test sequence of FIG. 7A at four (4) different ascorbate levels for a blood sample containing 550 mg/dL glucose at 42% Hct.

The ability to detect the QDI feature is made possible by application of an SRBP applied potential test sequence. The above examples are in no way intended to limit the invention to the use of a test sequence having a triangular SRBP waveform. Many other SRBP waveforms also can be utilized, such as trapezoidal, cosine and/or sine waveforms, which are shown in FIGS. 6A and 7A, respectively. Like the triangular SRBP waveform shown in FIG. 4A, these excitation potentials cycle between +450 mV and −450 mV using a slow ramp that is linear or defined by the cosine function. The plots shown in FIGS. 6B and 7B show the current response at each level of ascorbate after application of these alternative SRBP waveforms to a blood sample with 550 mg/dL glucose and 42% Hct. Analogous to the triangular SRBP waveform, both the trapezoidal and cosine SRBP waveforms produce a QDI and PDA feature for every +450-mV and −450-mV cycle. As shown in FIGS. 6B and 7B, the QDI feature qualitatively tracks the spiked ascorbate level, thus permitting quantification of test sample ascorbate.

In addition to the above, the measurement methods alternatively can use a hybrid test sequence to enhance overall SMBG system performance and capabilities. Exemplary hybrid test sequences include three blocks and integrate (1) a low-amplitude AC block at multiple frequencies for Hct and temperature compensation, (2) a first DC block having pulsed excitation and recovery potentials to improve performance and compensate for film thickness and process variations, use of recovery pulse information from pulsed DC excitation to further refine, and (3) a second DC block having SRBP waveforms for detecting and quantifying an interferent such as an antioxidant (e.g., ascorbate). The first three functionalities are realized with the first DC block shown in FIGS. 3A-B, and the fourth functionality is realized through a second DC block.

Figure 8A:
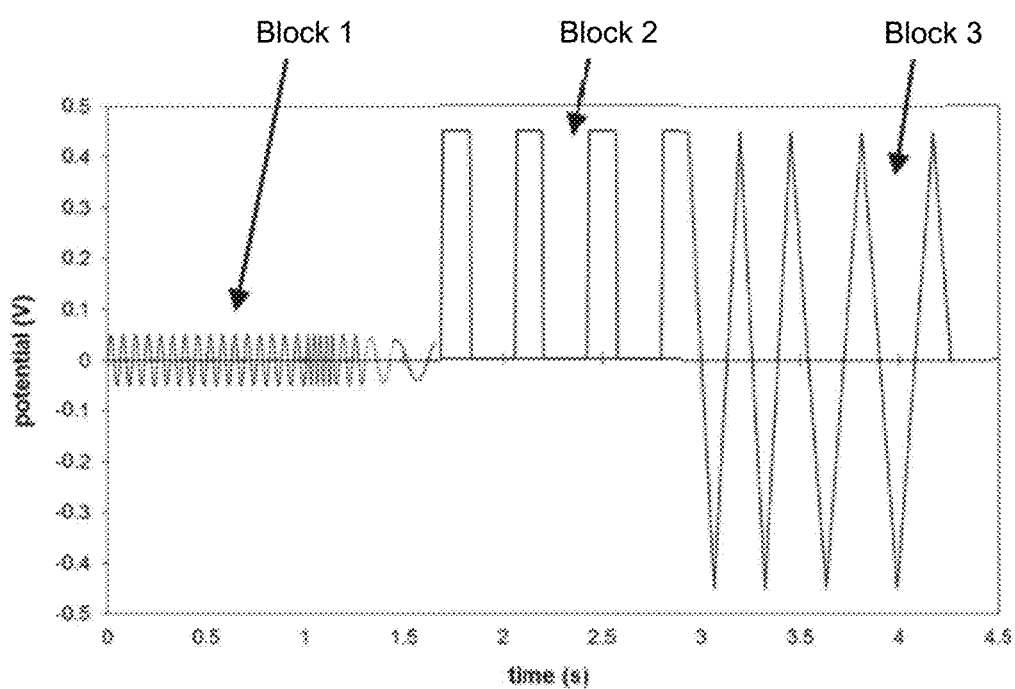
FIGS. 8A-B show alternative exemplary test sequences having three (3) blocks that may be employed by an analyte measurement device, apparatus or system, where
Figure 8B:
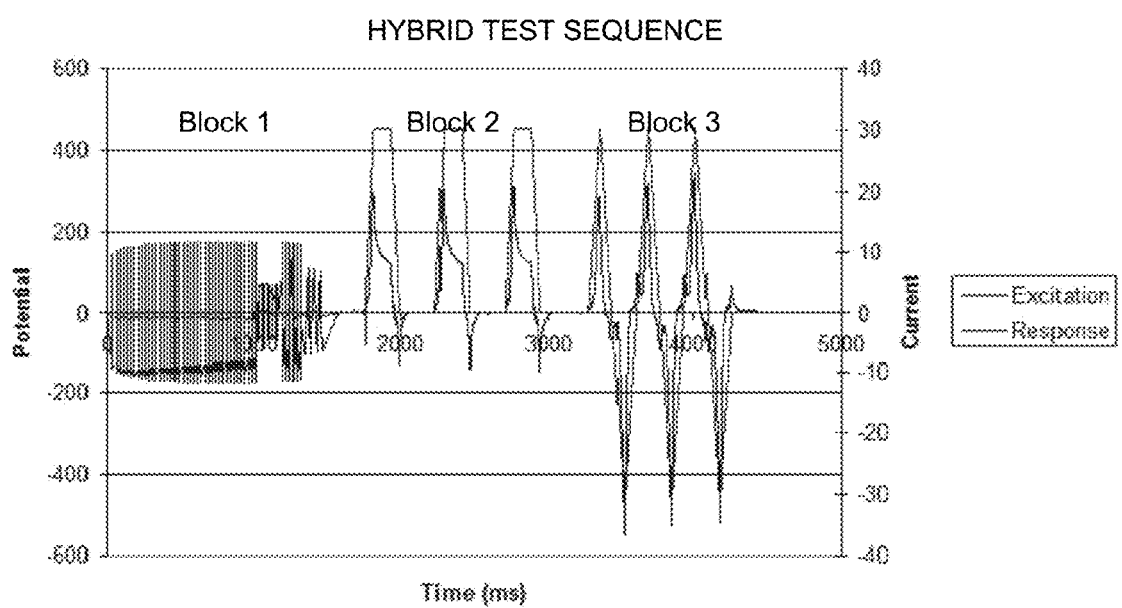

FIGS. 8A-B show an exemplary hybrid test sequence that includes Block 1, which is an AC block; Block 2, which is a first DC block; and Block 3, which is a second DC block. The test sequence of FIG. 8B was tested using a multi-channel, research-grade potentiostat but also may be adapted to be used in connection with SMBG devices, apparatuses, systems or even clinical systems.

In FIG. 8B, the AC block includes four (4) segments of low-amplitude AC excitation at three (3) distinct frequencies. The first DC block includes three (3) +450 mV DC excitation pulses and three (3) closed circuit 0 mV DC recovery pulses. Excitation and recovery current response information from these pulses can be used to determine a bG concentration. The second DC block includes the SRBP, which can be a triangular waveform designed to detect and quantify an antioxidant such as ascorbate. This hybrid test sequence integrates all four of the desired aspects as described above.

Figure 9:
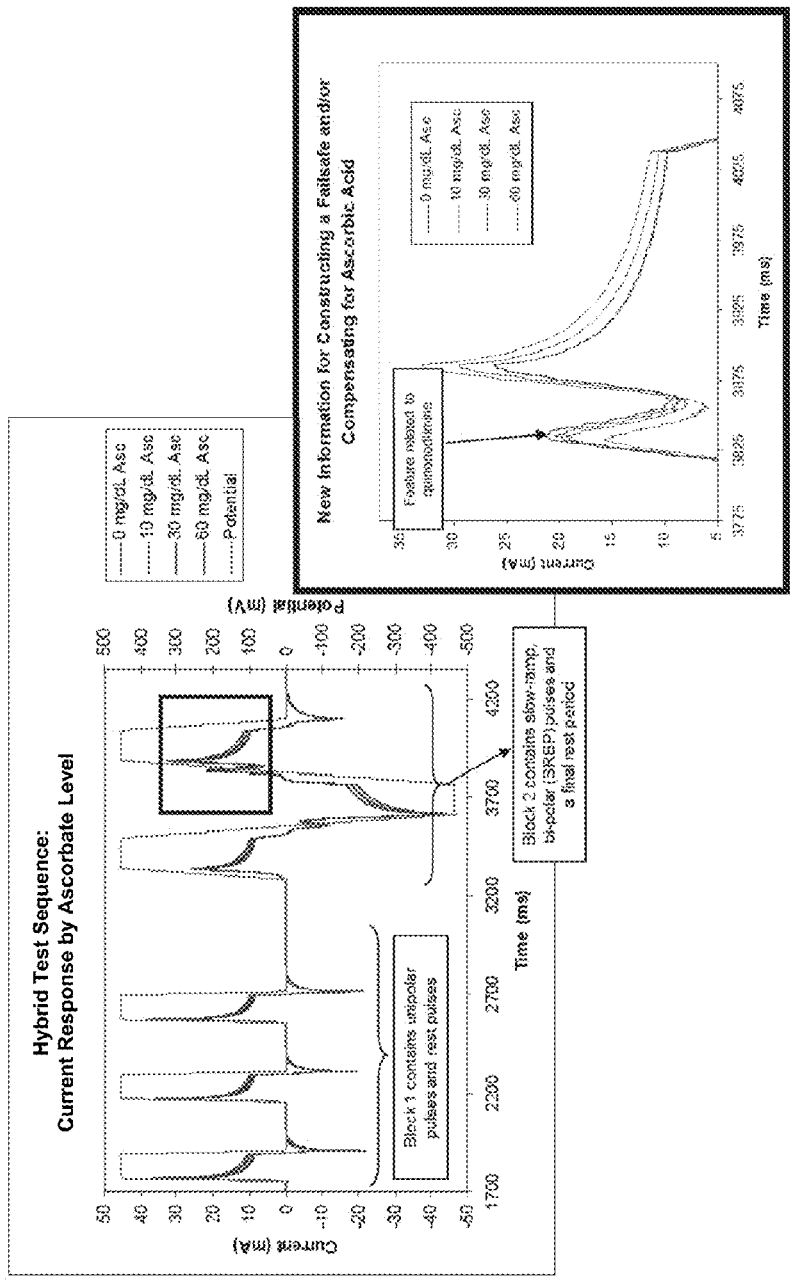
FIG. 9 shows exemplary DC blocks designed for measuring glucose (via Block 2 or DC Block 1) and for detecting and quantifying an antioxidant such as ascorbate (via Block 3 or DC Block 2) in which the current responses correspond to (4) four nominal blood samples containing different amounts of ascorbate.

FIG. 9 shows a more detailed view of the first DC block and the second DC block (i.e., the SRBP waveform) of FIG. 8B. The applied potential for the hybrid test sequence is shown in light grey. The first DC block referred to as Block 1, contains only positive +450 mV excitation pulses and about 0-mV recovery pulses. The second DC block, referred to as Block 2, includes the SRBP waveform, which also includes a final recovery period. The current responses in FIG. 9 correspond to four blood samples (at nominal glucose, Hct level and temperature) containing ascorbate levels of 0, 10, 30 and 60 mg/dL, respectively. The current response for Block 1 is used for quantitatively measuring glucose. Notice, however, that the magnitudes of the current responses from the positive excitation pulses increases as a function of ascorbate, even though the four samples contain the same amount of glucose. The increase is because the observed current is directly proportional to the amount of PDA present. By way of comparison, the QDI feature in Block 2 is decreasing as a function of ascorbate, while the PDA-related feature, analogous to the Block 1 responses, is increasing. This example illustrates that Block 2 contains new and different information that is not present in Block 1, and this information provides the basis for detecting and quantifying antioxidants such as ascorbate.

The hybrid test sequences shown in FIGS. 8A-B and 9 are not intended to limit the number of distinct DC test blocks, the shape or form of the applied DC potential for each block, the applied DC potential at the connection point(s) between blocks, or the placement and order of different DC blocks, relative to one another. Although these examples show that the DC blocks are connected (i.e., there is no discernable break between the last applied voltage of one block and the first applied voltage of the subsequent block), it also is possible that each DC block could be executed independently, separated by a break in applied voltage. These examples also assume that the current responses to the DC blocks are continuously followed by a closed-circuit; however, an open-circuit period between the current responses for each test block also could be used.

Additional work was performed to create, characterize and select an optimized hybrid test sequence including optimization of the ramp rates of any SRBP. Slower ramp rates produce wider QDI and PDA features that have lower current responses. In contrast, faster ramp rates produce narrower QDI and PDA features with higher current responses. Intuitively, there should be an optimal rate (or set of rates) that optimize(s) ease of detection (width) and quantitative information (height), thereby providing in the best quantitative prediction of ascorbate.

Various hybrid test sequences were created and evaluated. One group of hybrid test sequences contained multiple ramps; however, all ramps had the same rate. A second group of hybrid test sequences contained multiple ramps with up to three (3) different rates, which ranged from about 3 mV/msec to about 9 mV/msec.

An exemplary, optimized hybrid test sequence was created based upon the ability to quantitatively model ascorbate content using partial least squares (PLS) modeling, which is described in greater detail below. FIGS. 10A-F show examples of six (6) hybrid test sequences that produced good ascorbate prediction models. The first DC block of excitation and recovery pulses was identical in all the hybrid test sequences as was the AC block, which is not shown for clarity of illustration. Unlike the hybrid test sequences shown in FIGS. 8A-B and 9, the hybrid test sequences in FIG. 10 begin the second DC block, which is an SRBP waveform, from the end of the last excitation pulse in the first DC block, rather than from a recovery pulse. This maximized the number of excitation pulses in the first DC block (for glucose measurement and, at the same time, to minimize the time for all DC measurements (DC block 1 and DC block 2 (the SRBP block)).

Figure 10:
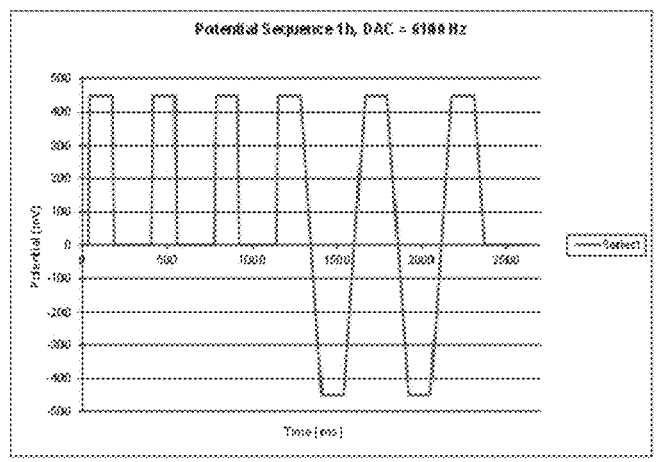
FIG. 10 a plurality of exemplary test sequences that produced quantitative models for an antioxidant such as ascorbate exclusively from an SRBP waveform (i.e., DC Block 2). Sequences B, D, E and F each contain up to three (3) different ramp rates in the Block 2 portion.
Figure 10:
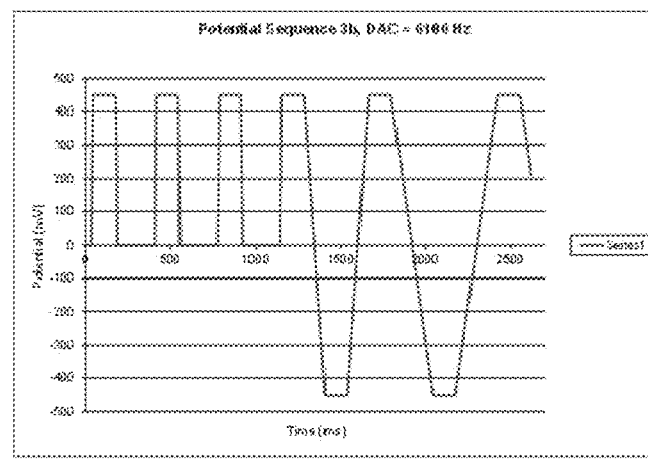
Figure 10:
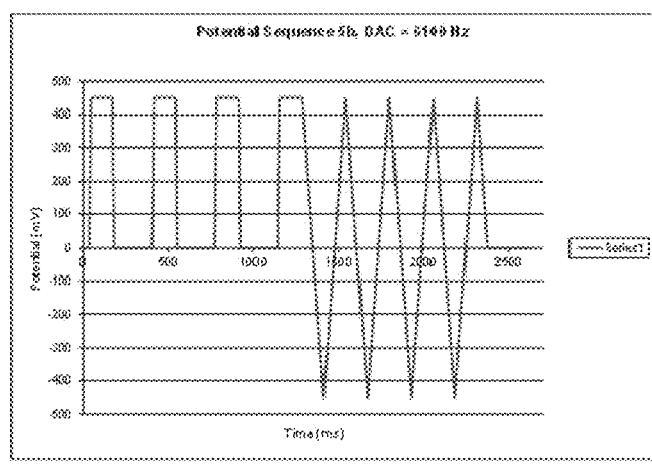
Figure 10:
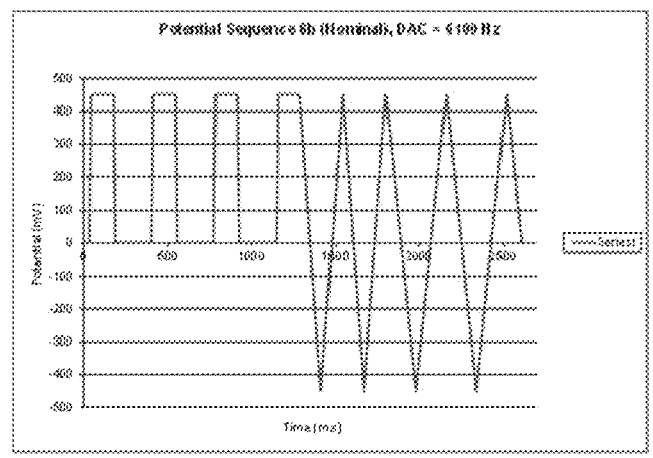
Figure 10:
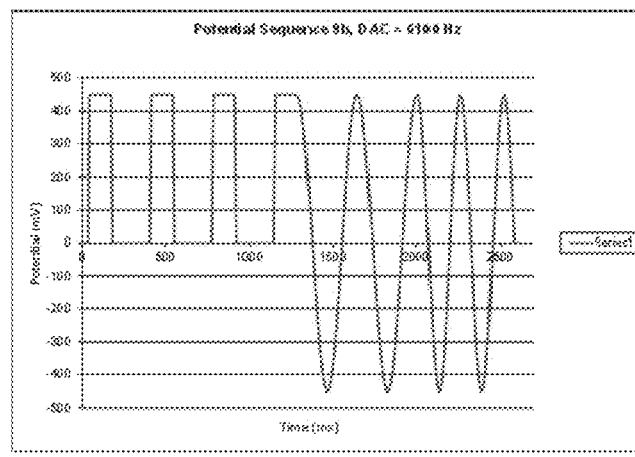
Figure 10:
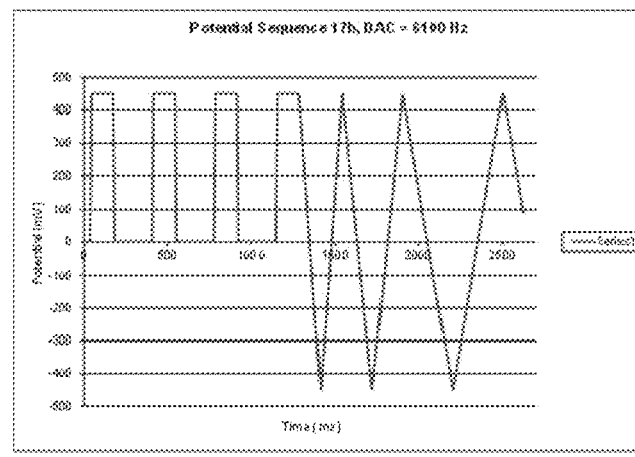

Based upon quantitative ascorbate prediction models, the hybrid test sequence shown in the bottom left plot in FIG. 10 was selected as the presently preferred hybrid test sequence and will be referred to herein as Sequence A. Sequence A contains two different ramp rates at about 7 mV/ms and about 5 mV/ms, respectively. DC Block 2 ends with a half-ramp (5 mV/ms) back to 0 mV, followed by a short recovery period. This example is not intended to limit the number of ramps or the rate(s) of the ramps in DC Block 2.

Using Sequence A, the inventive concepts described herein were further reduced to practice by establishing that they can be implemented on a hand-held SMBG meter. A new meter with a variable digital-to-analog converter (DAC) rate (minimum of about 4000 Hz) was used for convenience, as this functionality made it possible to execute any hybrid test sequence. Sequence A was executed at a DAC frequency of about 6100 Hz. The current response was sampled with an analog-to-digital converter (ADC) rate of about 900 Hz, corresponding to a data point every 1.11 msec. Fast sampling was used to fully characterize the shapes of current responses DC Blocks 1 and 2 and to enable the QDI feature to be resolved from the PDA feature in time. The resulting current responses were then digitally filtered to remove 50-Hz and 60-Hz power line noise.

Figures 11A, 11B:
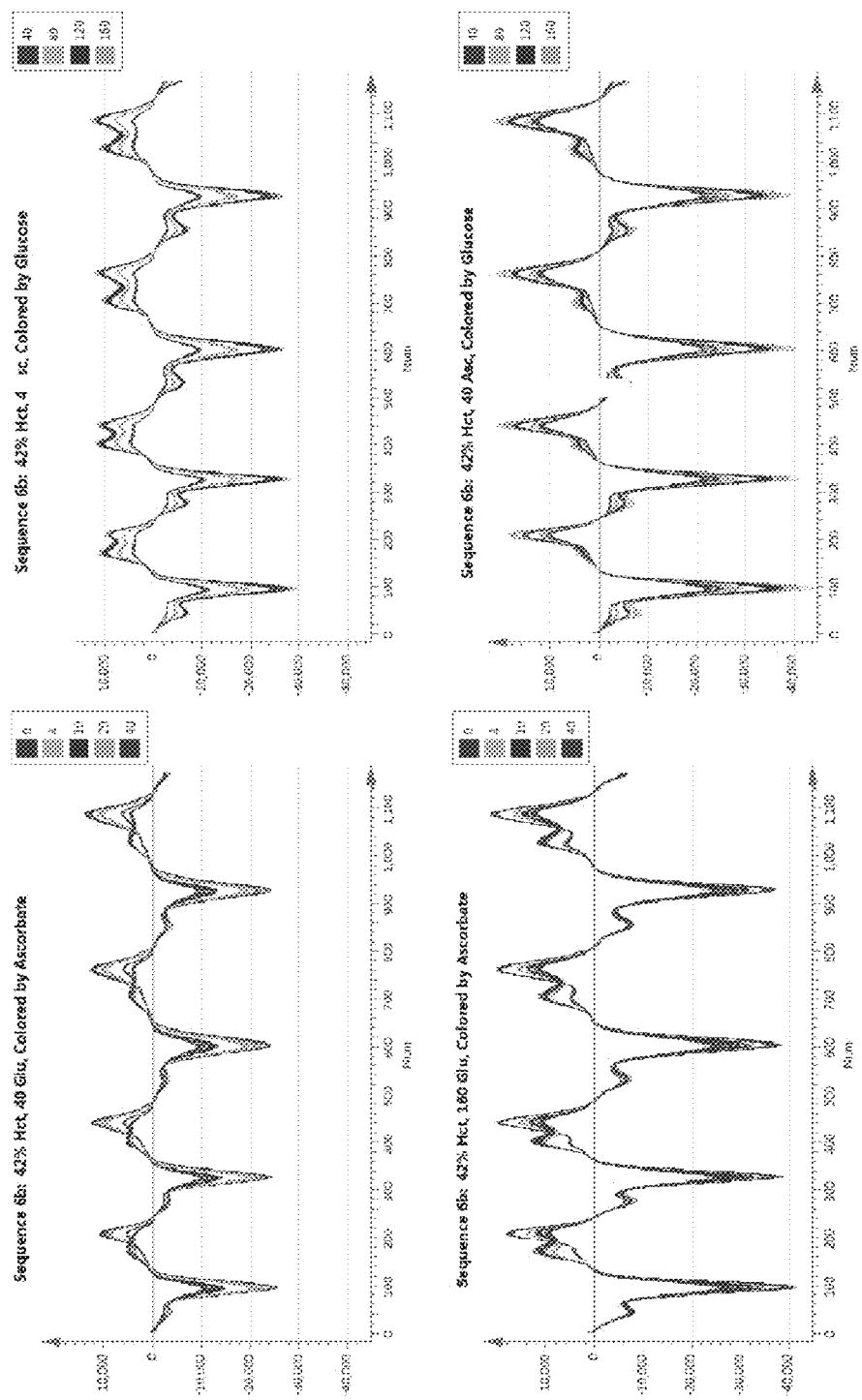
FIGS. 11A-B show exemplary DC Block 2 current responses obtained with test sequence A of FIG. 10, where the left two plots show the effects of changing ascorbate level at a fixed glucose level (top fixed at 40 mg/dL glucose and bottom fixed at 160 mg/dL glucose), and where the right two plots show the effects of changing glucose level at a fixed ascorbate level (top fixed at 4 mg/dL ascorbate and bottom fixed at 40 mg/dL ascorbate) and all samples were spiked blood samples and were measured eight (8) times.

FIGS. 11A-B show several examples of filtered current responses for DC Block 2. In FIG. 11A only information from DC Block 2 was used to detect and quantify ascorbate; therefore, the corresponding AC and DC Block 1 current responses were not shown. The two plots of FIG. 11A show the current responses for spiked blood samples containing 40 mg/dL glucose (top) and 160 mg/dL glucose (bottom). Both samples have a Hct level of 42% and were measured at room temperature. Each of the starting samples (with 0 mg/dL ascorbate) were spiked with 4, 10, 20 and 40 mg/dL of ascorbate, respectively, and each of these samples were measured eight (8) times using different SMBG biosensor on the new meter. The resulting current responses are colored by ascorbate level. The two plots of FIG. 11B demonstrate the effect of changing glucose levels at two fixed ascorbate levels of 4 mg/dL (top) and 40 mg/dL (bottom). The same starting blood sample was spiked to 40, 80, 120 and 160 mg/dL glucose. Each of these samples were then spiked with 4 mg/dL or 40 mg/dL ascorbate, respectively. All samples were measured eight (8) times using different SMBG biosensors on the new meter, and the resulting current responses are colored by changing glucose level. FIGS. 11A-B therefore provide clear illustrations that the DC Block 2 current responses contain adequate information for quantifying ascorbate and creating a failsafe.

To demonstrate proof of principle, two different datasets were created using blood samples, and the glucose and ascorbate levels were co-varied. All samples contained 42% Hct and were measured at room temperature using the new meter and Sequence A. The data were analyzed using PLS regression, which is a multivariate technique also known as projection to latent structures. PLS regression considers the covariance between a group of explanatory (independent) variables, herein termed X-variables, and one or more response (dependent) variables, herein referred to as Y-variables. Unlike multiple linear regression, PLS can be used when there are a large number of X-variables per observation, when there are more X-variables than observations, and/or when the X-variables are correlated. Explained simply, the PLS procedure forms new variables, or factors, that are linear combinations of the original X-variables and uses them for predictors of the Y variable(s). The factors are selected to describe the greatest variability in the X-matrix that also correlates with the variation in the Y-variable(s). In this work, PLS regression was performed using the Simca-P+ software package from Umetrics, Inc. (Kinnelon, N.J.). PLS models were constructed using the DC current values from the DC Block 2 current response as the X-variables; the response, or Y-variable, was the spiked ascorbate level. PLS models with only one Y-variable are often referred to as PLS1 models. Before analysis, all X and Y variables were independently centered by subtracting the mean.

Figure 12:
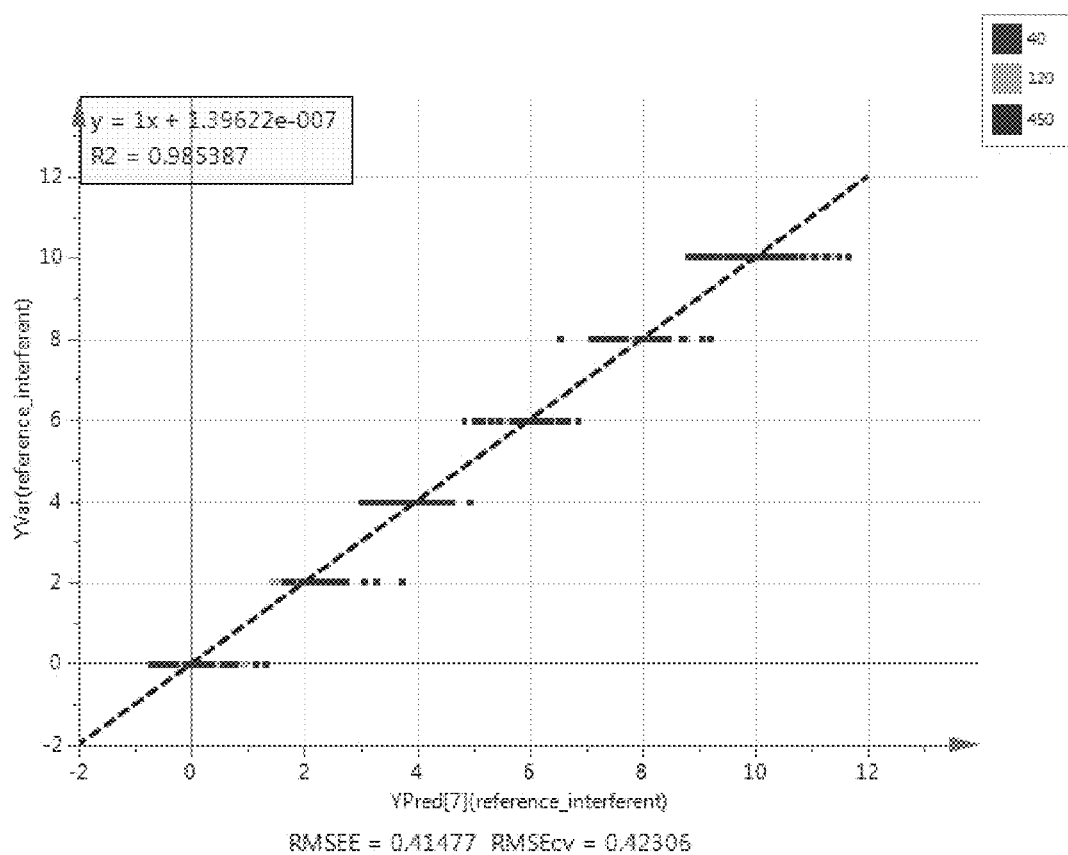
FIG. 12 shows actual Y values (i.e., admittance values; y-axis) vs. predicted Y values (x-axis) for PLS Model 1 (colored by target glucose level).

Here, dataset 1 included blood samples spiked to glucose levels of 40, 120 and 450 mg/dL, respectively. Each of these samples was then spiked to ascorbate levels of 2, 4, 6, 8 and 10 mg/dL, respectively. The final dataset contained 862 observations, which were used to construct PLS Model 1. The model contained 1173 X-variables, consisting of all of the measured values in DC Block 2 (in nA), and one Y-variable, which was the ascorbate level (in mg/dL). PLS Model 1 contained seven (7) significant factors, which were able to describe 98.5% ($R^2Y$) of the variability ascorbate level. The standard deviation of the Y-residuals was 0.413 mg/dL, and the root-mean-squared-error-of-estimate (RMSEE) of the model, a measure of precision, was 0.415 mg/dL. A plot of the actual Y-values versus the predicted Y-values is shown in FIG. 12. Observations are colored according to target glucose level, showing that PLS Model 1 provides excellent prediction of the ascorbate level across a wide range of glucose levels.

Figure 13:
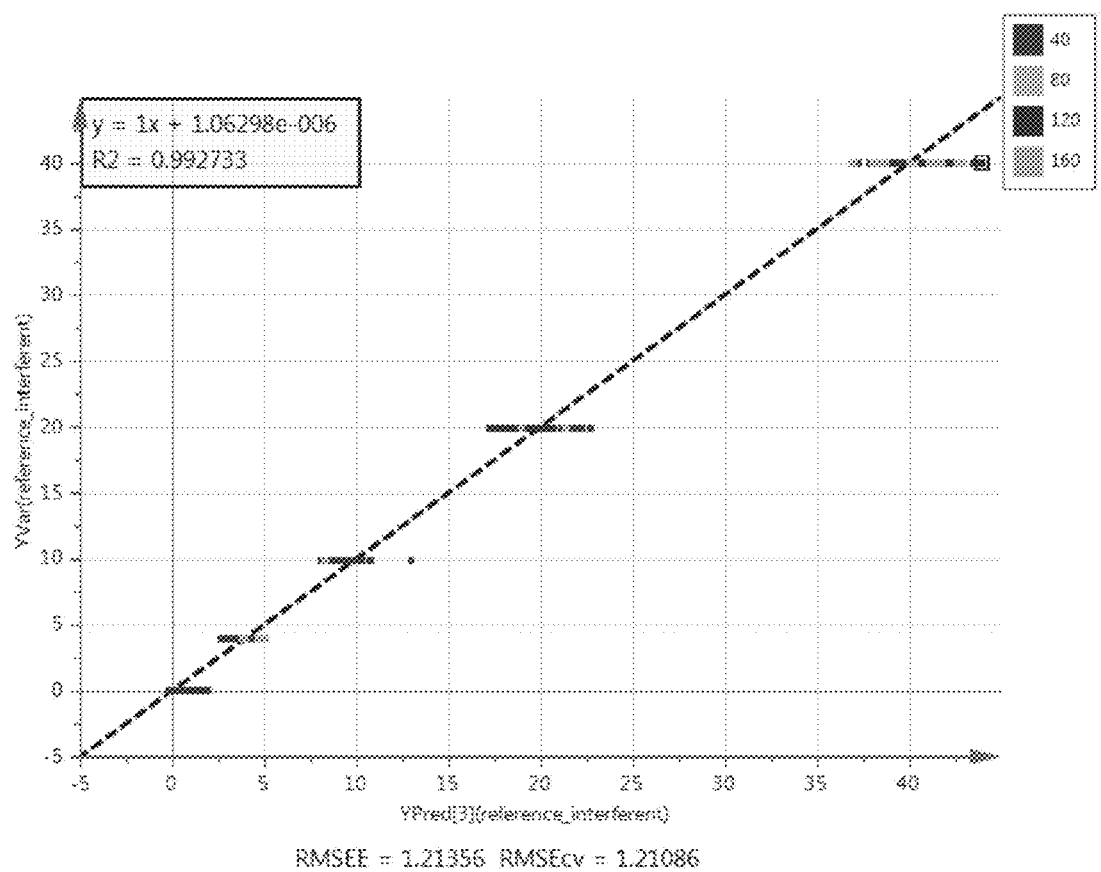
FIG. 13 shows actual Y values (y-axis) vs. predicted Y values (x-axis) for PLS Model 2 (colored by target glucose level).

Dataset 2 was designed to take a closer look at the glucose range below 170 mg/dL, using a wider range of ascorbate levels. Referring to a Parkes consensus error grid, a falsely-elevated bG reading in this range, caused by high ascorbate, may be more likely to produce an inappropriate medical response. Dataset 2 contained blood samples spiked to glucose levels of 40, 80, 120 and 160 mg/dL, respectively. Each of these samples was then spiked to ascorbate levels of 4, 10, 20 and 40 mg/dL, respectively. The final dataset contained 313 observations, which were used to construct PLS Model 2. As in the previous model, there were 1173 X-variables, consisting of all of the measured values in DC Block 2 (in nA), and one Y-variable, which was the ascorbate level (in mg/dL). PLS Model 2 contained three (3) significant factors, which were able to describe 99.3% ($R^2Y$) of the variability in ascorbate level. The standard deviation of the Y-residuals and the RMSEE for the model was 1.21 mg/dL. A plot of the actual Y-values versus the predicted Y-values is shown in FIG. 13. Observations are colored according to target glucose level. Like the previous model, PLS Model 2 also provides excellent prediction of the ascorbate level across the measured glucose range—but across a much wider ascorbate range.

Additional work has demonstrated that it is possible to create quantitative ascorbate models that also provide accurate prediction across varying Hct levels and temperature conditions. This methodology also works for fluidic samples with spiked ascorbate levels, should they be of interest for testing or quality control. It also should be noted that many different types of mathematical techniques can be used to build quantitative models, and different types of models may require different numbers of X-variables for optimal performance. The examples presented above are not intended to limit the invention to the use of PLS regression and/or to the use of all DC Block 2 current values for constructing functional models for predicting ascorbate levels.

Figure 14A:
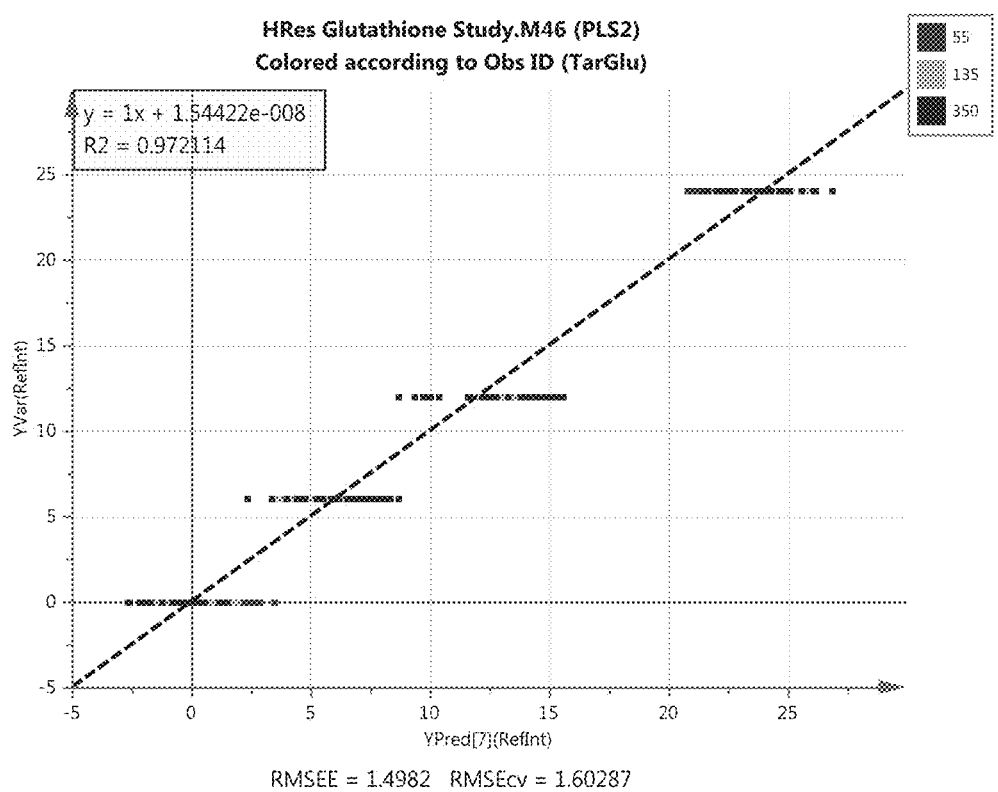
FIGS. 14A-B show quantitative models for another antioxidant—glutathione—as well as glucose, exclusively from the DC Block 2 data at three (3) glucose concentrations (55, 135 and 350 mg/dL) and four (4) glutathione concentrations (0, 6, 12 and 24 mg/dL).
Figure 14B:
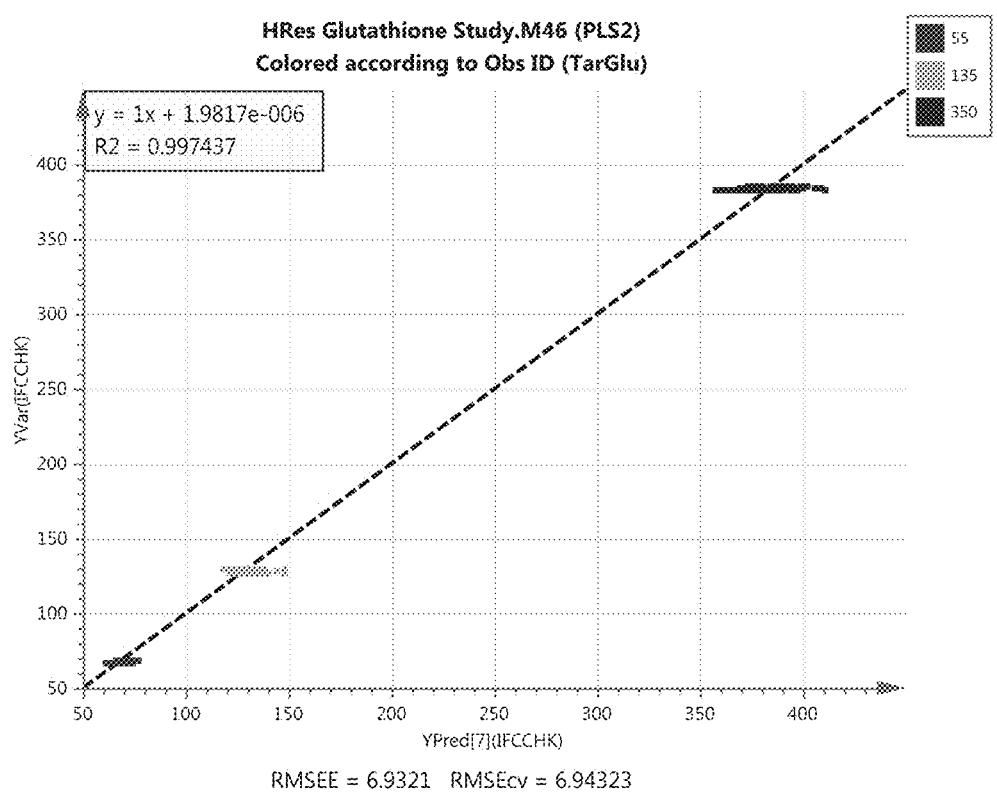
Figure 14C:
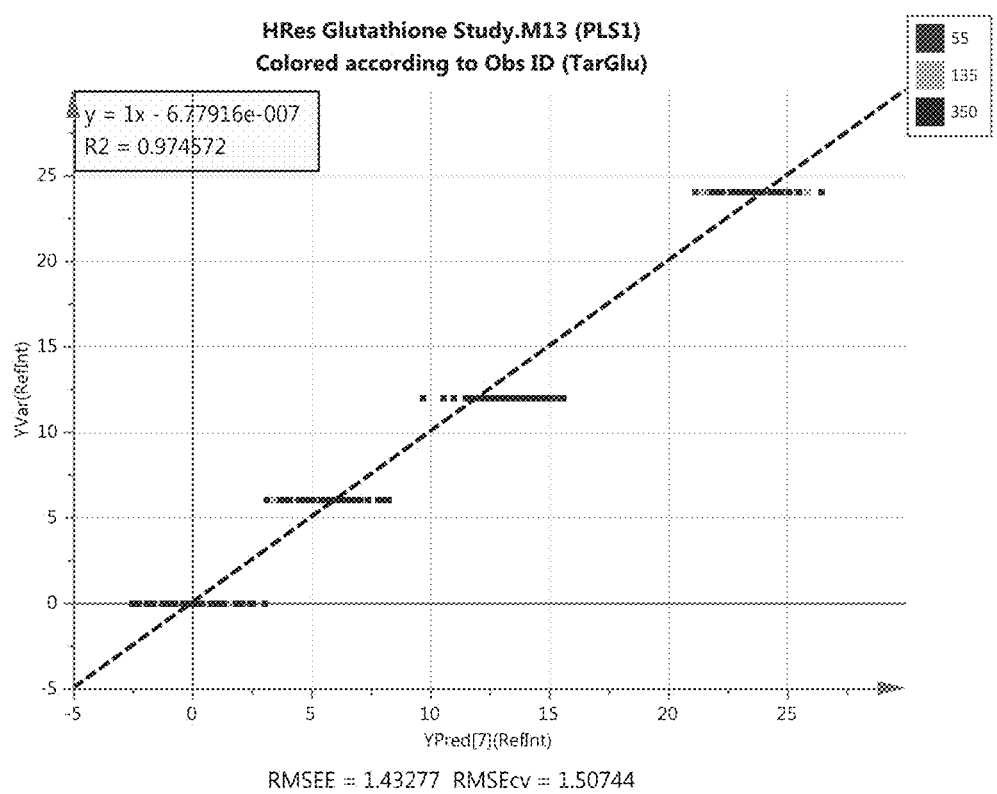
FIG. 14C shows an alternative glutathione prediction that further incorporates AC excitations for PLS Model 1. As above in FIGS. 12-13, the plots show actual Y values (y-axis) vs. predicted Y values (x-axis).

In addition to ascorbate, experiments were performed to similarly detect and quantify another antioxidant—glutathione. FIGS. 14A-B show quantitative models for glutathione, as well as glucose, built exclusively from DC Block 2 data (i.e., a response to a SRBP) as above at three (3) glucose concentrations (55, 135 and 350 mg/dL) and four (4) glutathione concentrations (0, 6, 12 and 24 mg/dL). Data were collected using a 3-block test sequence as described above. Plots of the actual Y-values versus the predicted Y-values is shown in FIGS. 14A-C. The best MVA PLS2 Model for simultaneously predicting glutathione (FIG. 14A) and glucose (FIG. 14B) used Block 2 DC variables only (no AC variables) and center scaling. In contrast, the best MVA PLS1 Model for quantitatively predicting glutathione alone (FIG. 14C) used Block 2 DC and all AC variables, along with Pareto scaling.

Figure 15A:
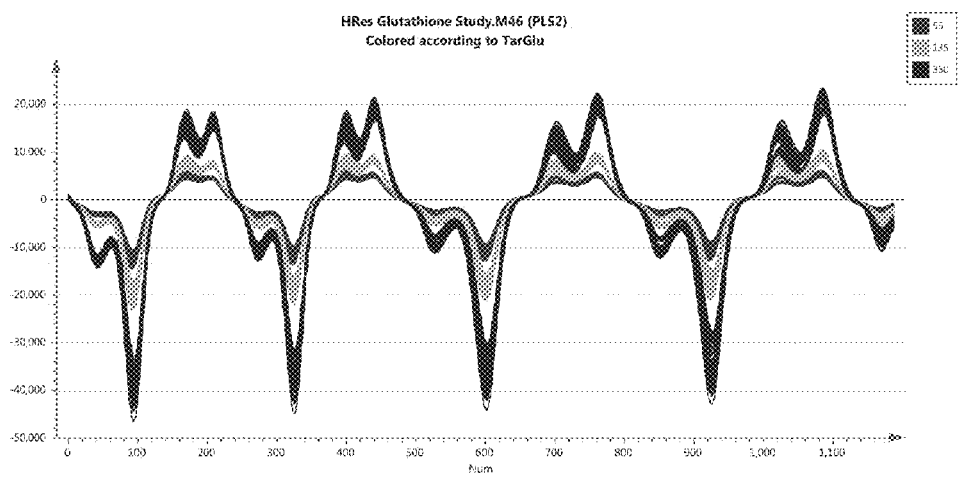
FIGS. 15A-B show DC Block 2 DC data for all observations colored by glucose (FIG. 15A) or by glutathione level (FIG. 15B) (x-axis is the order number of consecutive DC values starting at DC1157).
Figure 15B:
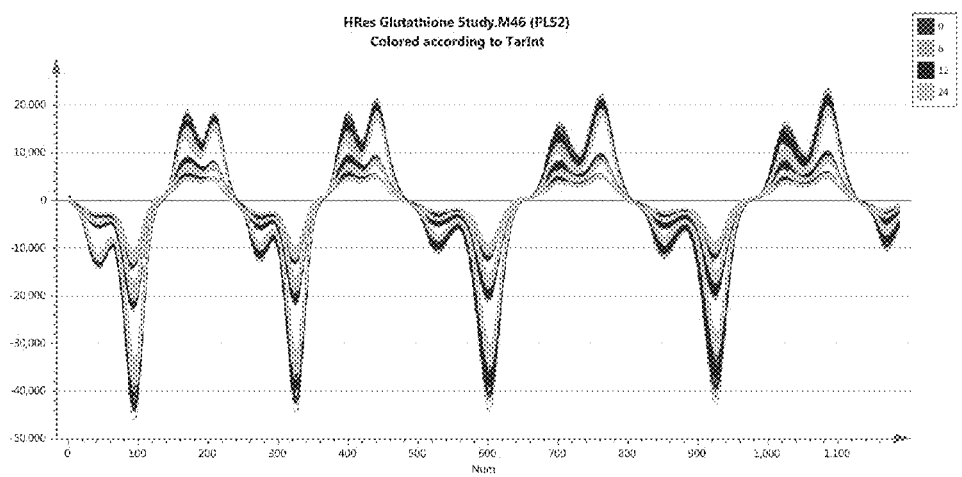

FIGS. 15A-B show several examples of filtered current responses for DC Block 2. The plot of FIG. 15A shows the current responses colored by glucose, whereas the plot of FIG. 15B shows the same set of current responses colored by glutathione. The two plots demonstrate the effect of changing glucose levels at two fixed ascorbate levels of 4 mg/dL (top) and 40 mg/dL (bottom). FIGS. 15A-B therefore provide clear illustrations that the DC Block 2 current responses contain adequate information for quantifying glutathione and even glucose.

Figure 16:
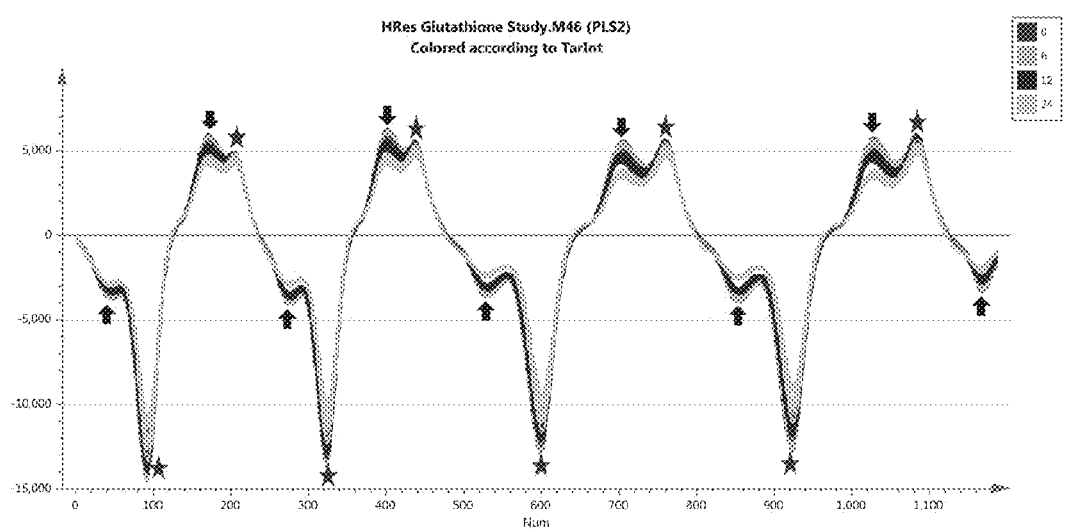
FIG. 16 shows DC Block 2 data for all observations in which the target glucose concentration=55 mg/dL. Quinonediimine (QDI) peaks are noted with arrows; and phenylenediamine (PDA) peaks are noted with stars.

FIG. 16 shows a plot of DC Block 2 data for all observations in which the target glucose concentration was 55 mg/dL. QDI peaks/features are noted with arrows, and PDA peaks/features are noted with stars. As observed for ascorbate, increasing concentrations of glutathione cause a decrease in the magnitude of the QDI feature.

However, unlike ascorbate, which produces a corresponding increase in the PDA feature (thus leading to a falsely-elevated glucose concentration), glutathione produces a very small, but still discernable, decrease in the PDA feature. It is believed that this difference can be attributed to the one-electron glutathione reaction with QDI is different from the two-electron reaction of ascorbate and QDI. As such, it appears that QDI is prevented from forming additional PDA.

These results illustrate that all antioxidants do not produce the same level of risk to the reported glucose concentration. Since the glucose concentration is determined using PDA information only, and since glutathione does not cause significant changes in PDA, there is little impact on the reported glucose concentration when the antioxidant is glutathione. Higher levels of glutathione (e.g., 50, 100 or 200 mg/dL) are not believed to behave any differently.

Because ascorbate and glutathione do not cause the same changes, it is possible to distinguish the two from a pattern recognition perspective.

The ability to quantify antioxidant levels, such as ascorbate levels, based upon a hybrid test sequence containing an SRBP, as demonstrated by the foregoing examples, can be used in two different ways: (1) to provide compensation, or correction, to a calculated bG value before reporting; and (2) to construct a failsafe that can be used to prevent reporting of an inaccurate bG value if the ascorbate level is above a pre-determined level. The ability to quantify ascorbate also can be logically combined with the capability for qualitative detection of ascorbate (or other interfering substances that reduce QDI); this is the "chemistry health" failsafe described earlier. One practical example of how these different capabilities, indicated in brackets below, could be combined in a handheld SMBG meter is in accordance with the following processes:

a. determine whether the expected QDI feature is present. If not, then stop the test and send an error code (chemistry health failsafe);

b. predict the amount of glucose present, by using a glucose-specific algorithm that considers DC Block 1 information and/or additional information from DC Block 2;

c. predict the amount of antioxidant present using an antioxidant-specific algorithm based upon DC Block 2 (capability to quantify the antioxidant). If the amount of antioxidant is above a pre-determined threshold, do not report a glucose reading and send an error code (i.e., antioxidant failsafe); and d. optionally use the reported antioxidant level to adjust, or correct, the glucose value calculated in Step 2. This would require construction of an additional model that relates the error in the predicted bG to the predicted antioxidant level. This model would then provide a correction factor that could be used to adjust the calculated bG value from Step 2 before it is reported. Alternatively, a multivariate method that simultaneously models both glucose and antioxidant, using information from anywhere in the AC and DC current responses, could be used to produce a second, corrected bG value, which would be reported instead of the value calculated in Step 2.

It is should be understood that this logical flow of events is presented as an example and is not intended to limit or dictate the method for using the practical aspects of the invention This disclosure has described unique capabilities for detecting and quantifying an antioxidant or even a reducing agent that can be readily incorporated into a handheld SMBG meter and can be used to prevent reporting of inaccurate bG values to individuals having diabetes and undergoing various types of antioxidant therapy. The measurement methods disclosed herein can be used with amperometric SMBG systems that use at least one DC block in which the applied voltage is ramped at a rate that makes it possible to distinguish the electrochemical signature(s) associated with the redox mediator. The ramped voltage may be linear or follow other functional forms, such as a sine or cosine wave. The methodology for detecting ascorbate is applicable to any electrochemical system containing a mediator that is reduced by an antioxidant or other reducing agent and which has a unique voltage-current signature that differs from that of the enzyme.

While the embodiments described above utilize both DC Block 1 and DC Block 2 current response information to provide glucose (or another analyte) and antioxidant concentration determinations, in other embodiments glucose and ascorbate can both be predicted from the DC Block 2 alone.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

The invention claimed is:

1. A method of electrochemically measuring an analyte in a fluid sample in the presence of an antioxidant, the method comprising the steps of:
applying an electrical test sequence to an electrochemical biosensor, the biosensor comprising:
an electrode system,
a reagent including a redox mediator in electrical communication with the electrode system, and
a receptacle configured to contact the fluid sample provided to the biosensor,
with the fluid sample in fluidic contact with the reagent, wherein the test sequence comprises at least two direct current (DC) blocks, wherein a first DC block includes a slow-ramp bi-polar (SRBP) waveform having at least one SRBP recovery potential, wherein a second DC block includes a sequence alternating between at least one excitation potential and at least one recovery potential, and wherein a closed circuit condition of the electrode system is maintained during the at least two DC blocks;
measuring current response information to the first DC block, including information from the at least one SRBP recovery potential;
measuring current response information to the second DC block, including the at least one excitation potential and the at least one recovery potential;
evaluating quantitatively a level of the antioxidant present in the fluid sample based at least in part upon current response information to the SRBP waveform; and
determining an analyte concentration of the fluid sample based at least in part upon current response information from the excitation current response and the recovery current response, the determining compensating for the antioxidant.

2. The method of claim 1 further comprising the step of displaying a failsafe if the level of the antioxidant is above a predetermined threshold.

3. The method of claim 2, wherein the failsafe is an error code or a specific failsafe message.

4. The method of claim 1, wherein the redox mediator is a nitrosoanaline (NA)-derived redox mediator.

5. The method of claim 4, wherein the NA-derived redox mediator is N,N-bis(hydroxyethyl)-3-methoxy-4-nitrosoanaline hydrochloride.

6. The method of claim 1, wherein the SRBP waveform is at least one of a triangular potential waveform, a trapezoidal potential waveform or a sinusoidal potential waveform.

7. The method of claim 1, wherein the SRBP waveform alternates between about −450 mV to about +450 mV at equal ramp rates, or wherein the SRBP waveform alternates between about −450 mV to about +450 mV at two different ramp rates.

8. The method of claim 7, where the ramp rates are between about 3 mV/msec and about 9 mV/msec.

9. The method of claim 1, wherein the second DC block alternates between about +450 mV to about 0 mV for the at least one excitation potential to the at least one recovery potential.

10. The method of claim 1, wherein the second DC block is applied prior to the at least one DC block.

11. The method of claim 1, wherein the test sequence further comprises an alternating current (AC) block.

12. The method of claim 11, wherein the test sequence includes in ordered sequence the AC block, the second DC block, and the first DC block.

13. The method of claim 1, wherein the antioxidant is ascorbate.

14. The method of claim 1, wherein the biosensor is configured for operation in connection with a self-monitoring blood glucose (SMBG) system.

15. The method of claim 1, wherein the biosensor is configured for operation in connection with a self-monitoring blood ketone (SMBK) system.

16. A method of electrochemically measuring an analyte in a fluid sample that may have one or more interferents, the method comprising the steps of:
applying an electrical test sequence to an electrochemical biosensor, the biosensor comprising:
an electrode system,
a reagent including a redox mediator in electrical communication with the electrode system, and
a receptacle configured to contact the fluid sample provided to the biosensor,
with the fluid sample in fluidic contact with the reagent, wherein the test sequence includes a first signal component configured to provide a current response varying as a function of concentration of one or more interferents in the fluid sample, and wherein the test sequence further a second signal component comprising a sequence of potential pulses alternating between an excitation potential configured to produce an excitation current response associated with an electrochemical reaction of an analyte and the reagent and a recovery potential configured to produce a recovery current response associated with a closed circuit recovery of the biosensor;
performing a reagent chemistry health failsafe check based upon an evaluation of the current response to the first signal component indicating the concentration of the one or more interferents; and
determining concentration of the analyte based upon the excitation current response information and the recovery current response information to the second signal component.

17. The method of claim 16, wherein the first signal component is configured to provide a current response varying as a function of concentration of one or more interferents in the fluid sample comprises a slow-ramp bi-polar (SRBP) waveform.

18. The method of claim 17, wherein the SRBP waveform is at least one of a triangular potential waveform, a trapezoidal potential waveform or a sinusoidal potential waveform.

19. The method of claim 16, wherein the redox mediator is a nitrosoanaline (NA)-derived redox mediator.

20. The method of claim 19, wherein the NA-derived redox mediator is N,N-bis(hydroxyethyl)-3-methoxy-4-nitrosoanaline hydrochloride.

21. The method of claim 16 further comprising the step of:
evaluating quantitatively a level of the one or more interferents present in the fluid sample based at least in part upon current response information of the current response, wherein at least one of the one or more interferents is an antioxidant.

22. The method of claim 21, wherein the antioxidant is ascorbate.

23. The method of claim 16, wherein the determining concentration of the analyte step compensates for the at least one interferent.

24. The method of claim 16, wherein if the performing the reagent chemistry health failsafe check step indicates a potential for a clinically significant bias, the analyte concentration is not displayed but instead is failsafed with an appropriate message of suspected interference, reagent layer failure, or even a general biosensor failure.

25. A method of electrochemically measuring an analyte in a fluid sample and providing an antioxidant failsafe, the method comprising the steps of:

evaluating a level of the antioxidant present in the fluid sample based at least in part upon current response information to a slow-ramp bi-polar (SRBP) waveform applied under a closed circuit condition, wherein the SRBP waveform alternates between about −450 mV to about +450 mV at equal ramp rates, or wherein the SRBP waveform alternates between about −450 mV to about +450 mV at different ramp rates, wherein the ramp rates are between about 3 mV/msec and about 9 mV/msec, and wherein a failsafe is displayed if the level of the antioxidant is above a predetermined threshold.

26. The method of claim 25, wherein the failsafe is an error code or a specific failsafe message.

27. The method of claim 25, wherein the failsafe is based upon a presence or absence of an expected redox mediator status.

28. The method of claim 27, wherein the redox mediator is a nitrosoanaline (NA)-derived redox mediator.

29. The method of claim 28, wherein the NA-derived redox mediator is N,N-bis(hydroxyethyl)-3-methoxy-4-nitrosoanaline hydrochloride.

30. The method of claim 29, wherein the expected redox mediator status is a quinonediimine (QDI) feature, and wherein the QDI feature is absent.

31. The method of any claim 25, wherein the SRBP waveform is at least one of a triangular potential waveform, a trapezoidal potential waveform or a sinusoidal potential waveform.

32. The method of claim 25, wherein the antioxidant is ascorbate.

33. The method of claim 32, wherein the predetermined threshold is about 3 mg/dL of ascorbate in the fluid sample.

* * * * *